US011597903B2

(12) United States Patent
Hiller et al.

(10) Patent No.: US 11,597,903 B2
(45) Date of Patent: Mar. 7, 2023

(54) CELL-CONTROLLED PERFUSION IN CONTINUOUS CULTURE

(71) Applicant: Boehringer Ingelheim International GmbH, Ingelheim am Rhein (DE)

(72) Inventors: Gregory Walter Hiller, Wakefield, MA (US); Matthew Paul Gagnon, Medford, MA (US); Ana Maria Ovalle, Medford, MA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/577,415

(22) PCT Filed: May 27, 2016

(86) PCT No.: PCT/US2016/034570
§ 371 (c)(1),
(2) Date: Nov. 28, 2017

(87) PCT Pub. No.: WO2016/196261
PCT Pub. Date: Dec. 8, 2016

(65) Prior Publication Data
US 2018/0171279 A1 Jun. 21, 2018

Related U.S. Application Data

(60) Provisional application No. 62/246,774, filed on Oct. 27, 2015, provisional application No. 62/199,388, filed on Jul. 31, 2015, provisional application No. 62/168,297, filed on May 29, 2015.

(51) Int. Cl.
*C12N 5/00* (2006.01)
*C12M 1/00* (2006.01)
*C12M 1/34* (2006.01)

(52) U.S. Cl.
CPC ............ *C12M 29/10* (2013.01); *C12M 41/26* (2013.01); *C12N 5/0018* (2013.01); *C12N 5/0062* (2013.01); *C12N 2500/60* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| 5,122,469 A * | 6/1992 | Mather ................ C12N 5/0037 435/383 |
| 2004/0259240 A1* | 12/2004 | Fadden .................. C12M 47/10 435/297.3 |

| 2006/0121568 A1* | 6/2006 | Drapeau ................ C07K 16/18 435/69.1 |
| 2009/0042253 A1 | 2/2009 | Hiller |
| 2011/0047314 A1 | 2/2011 | Pogor et al. |
| 2011/0104734 A1 | 5/2011 | Croughan et al. |

FOREIGN PATENT DOCUMENTS

| EP | 0567738 A2 | 3/1993 |
| WO | 2004104186 A1 | 12/2004 |

OTHER PUBLICATIONS

Pollock et al. "Fed-batch and perfusion culture processes: economic, environmental, and operational feasibility under uncertainty." Biotechnology and Bioengineering 110.1 (2013): 206-219 (Year: 2013).*
Gagnon, Matthew, et al. "High-End pH-Controlled Delivery of Glucose Effectively Suppresses Lactate Accumulation in CHO Fed-Batch Cultures" (2011, Biotechnology and Bioengineering, vol. 108, No. 6, 1328-1337.
Ozturk, S.S. et al. "Real-Time Monitoring and Control of Glucose and Lactate Concentrations in a Mammalian Cell Perfusion Reactor" (1997) Biotechnology and Bioengineering, vol. 53, No. 4, 372-378.
Tsao, T.S. et al. "Monitoring Chinese hamster ovary cell culture by the analysis of glucose and lactate metabolism" (2005) Journal of Biotechnology, vol. 118, 316-327.
International Search Report for PCT/US2016/034570 dated Oct. 20, 2016.
Lactate-GloTM Assay, Technical Manual, Promega Corporation, 2017.
Li et al., "Feeding Lactate for CHO Cell Culture Processes: Impact on Culture Metabolism and Performance", Nov. 28, 2011, Biotechnology and Bioengineering, vol. 109, No. 5, pp. 1173-1186.
Liu et al., "Downstream of Biotechnology-cell culture, isolation, purification and analytical detection", Chemical Industry Press, 1993, p. 33-36.
Recommended Media Types for Common Cells, Thermo Fisher Scientific, 2020.
Wu et al., "Practical Medical Cell Culture Techniques", 2010, Zhongshan University Press.

* cited by examiner

*Primary Examiner* — Emily A Cordas
(74) *Attorney, Agent, or Firm* — Mary Breen Smith

(57) ABSTRACT

Methods of protein production in continuous perfusion mammalian cell culture bioreactors are provided. Methods for continuous perfusion culture by allowing cells to self-regulate the rate of addition of perfusion medium to the bioreactor via a pH change are presented. Compositions comprising the perfusion medium as well as the process advantages of using hi-end pH control of perfusion or HIPCOP are also presented.

8 Claims, 25 Drawing Sheets

| CELL LINE | TOTAL VOL. USED DURING PERFUSION (REACTOR VOLUMES USED FROM DAYS 0-4) | VOL. OF FEED DURING FED-BATCH (REACTOR VOLUMES) | MAXIMUM VOLUMETRIC PRODUCTIVITY ACHIEVED (grams/L/day) |
|---|---|---|---|
| A | 1.6 | 0.4 | 1.04 |
| B | 1.4 | 0.4 | 1.00 |
| C | 1.4 | 0.4 | 1.16 |
| D | 1.8 | 0.3 | 0.56 |

*FIG. 8*

| OVERALL VOLUMETRIC PRODUCTIVITY OF PROCESS (grams/L/day) | TOTAL VOL. OF PERFUSION MEDIUM USED DURING HIPCOP PHASE OF PERFUSION- DAY 1-6 (REACTOR VOLUMES) | TOTAL VOL. OF HIGHLY CONCENTRATED PERFUSION MEDIUM USED FROM DAY 6-17 (REACTOR VOLUMES) | TOTAL VOL. OF SALINE DILUENT USED FROM DAY 6-17 (REACTOR VOLUMES) |
|---|---|---|---|
| 1.51 | 3.8 | 1.73 | 4.0 |

CELL-CONTROLLED PERFUSION IN CONTINUOUS CULTURE

RELATED APPLICATIONS

This application claims the priority benefit of U.S. Provisional Application Nos. 62/168,297, filed May 29, 2015; 62/199,388, filed Jul. 31, 2015 and 62/246,774, filed Oct. 27, 2015. The entire content of each of the above applications is incorporated herein by reference as though fully set forth herein.

FIELD OF THE SUBJECT TECHNOLOGY

The subject technology relates to methods of protein production in cultured animal cells, preferably mammalian cells, using continuous perfusion cell culturing in a bioreactor.

BACKGROUND OF THE SUBJECT TECHNOLOGY

Microorganisms or single cells of multicellular species are grown in various ways, including batch, fed-batch, continuous cultures, continuous cultures with cell retention (perfusion) or combinations thereof. Batch cultures require that a microbe or cell, for example, yeast, bacteria or fungal inoculums, is grown in a closed culture system on a limited or constant amount of growth medium. In batch cultures, there are a number of growth phases that the microbe passes through before cell death due to consumption of nutrients in the medium and production of toxic metabolites. Fed-batch cultures are similar to batch culture methods except that the batch culture is fed with nutrient medium in a fermentor or bioreactor without removing growth culture or growth products. As expected, the volume of the culture fluid in the bioreactor increases over time but typically high cell densities are achieved in this method of culture as compared to batch culture. Continuous cultures, in which the bioreactor volume remains constant and fresh medium is added and culture fluid is removed continuously, are another operational mode. In such a culture additional cell division is likely to occur, particularly if there is a continuous removal of cells from the bioreactor. Continuous cultures can also employ a cell retention device which retains all or nearly all cells within the bioreactor. When cell retention is employed cell densities can be much higher in the bioreactor as higher rates of medium flow in and out of the bioreactor (higher perfusion rates) are possible without the risk of cell washout. It is also possible to combine modes of bioreactor operation.

Due to the limits of feed volume addition and the problem of amino acid counter ion, miscellaneous osmolyte, and cell growth inhibitor accumulation, the fed-batch mode of bioreactor operation of cell production, for example, Chinese hamster ovaries (CHO) cell production, of protein therapeutics is inherently limited with respect to the cell densities and productivities that are achievable. Lactic acid, a growth inhibitor secreted during cell growth, is especially problematic. Lactic acid is produced by the breakdown of glucose in the cells and causes the bulk pH to drop as its concentration increases. Although lactic acid can be neutralized to lactate with the addition of a base titrant during cell culture, the addition of base results in large changes in osmotic strength of the growth medium due to ion accumulation. Both the rise in osmotic strength due to lactate accumulation, and the lactate ion itself can ultimately slow cell growth and can cause loss of cell productivity. Other efforts to reduce lactic acid formation include limiting glucose concentration, substituting alternative six-carbon sugars such as galactose, fructose, or mannose for glucose, and/or manipulating certain enzymes or substrate membrane transporters during cell culturing. More recently, high-end pH-controlled delivery of glucose has been shown to limit lactic acid secretion during fed-batch culture (Luan et al., U.S. Pat. No. 7,429,491 B2 and Gagnon et al., Biotechnol. Bioeng., 2011; 108: 1328-1337).

Continuous or perfusion culture with cell retention can overcome some of these limitations, but suffers from the disadvantages of large volume media consumption, long times to reach peak cell densities and complications with cell retention devices. Therefore, there still remains a need for an alternative culture method that overcomes the limitations associated with fed-batch and/or conventional continuous perfusion cultures.

SUMMARY OF THE SUBJECT TECHNOLOGY

The goal of this subject technology is to overcome current limitations in continuous perfusion cell culture and provide alternative methods to optimize cell growth and viability.

A method of continuous culture is described that overcomes many of the limitations outlined above and the method utilizes a unique technology which allows cells to control their own rate of perfusion with continuous feedback, i.e., self-regulating cells. The terms "hi-end pH control of perfusion or HIPCOP" are used to describe the process by which cells control their own rate of perfusion. Volumetric productivities of equal to about, or greater than, 1 gram/L/day for moderate specific productivity cell lines are achieved with very modest medium volumes, comparatively simple bioreactor operations, and a batch length that fits in a standard fed-batch window. The volumetric productivity achieved is more than double what one might achieve with the same cell line in an optimized fed-batch culture.

In its broadest aspect, the subject technology relates to a continuous perfusion culture process comprising monitoring pH in a cell culture in perfusion bioreactor with a pH controller or sensor, activating a medium perfusion pump delivering fresh medium and a permeate perfusion pump removing a nearly equivalent volume of permeate when the pH increases above a setpoint or predetermined value, and deactivating the medium perfusion pump and permeate perfusion pump when the pH decreases below a setpoint or predetermined value. In other words, in an embodiment, the subject technology relates to a continuous perfusion culture process, including: (a) monitoring pH in a cell culture with a pH sensor; (b) delivering fresh medium and removing permeate when the pH is above a predetermined value; and (c) deactivating the medium delivery and the permeate removal when the pH decreases below the predetermined value. In essence, the pH change in the cell culture medium is a result of the cell metabolism which then triggers the perfusion process. Alternatively, the method may be described as a cell-controlled perfusion process without a need to measure glucose concentration. The pH trigger for turning on and off the perfusion pumps, fresh medium and permeate pumps, is set at a predetermined value. This predetermined value is about pH 7 (e.g., between 6.8-7.4). The medium comprises glucose, L-lactate and a specified ratio of amino acid to glucose. According to this subject technology, the activation and deactivation of the medium perfusion pump and the permeate perfusion pump may occur simultaneously or independently. Also, the permeate may be cell-free or may contain cells.

The described method also comprises adding L-lactate to a fresh perfusion medium used in the continuous culture process. In an embodiment, the L-lactate present in the perfusion medium is in an amount of about 0.1 g/L to about 7.0 g/L. More preferably, the L-lactate present in the perfusion medium is in an amount of about 1 to about 4 g/L, about 1 to about 3 g/L, or about 1 to about 2.5 g/L. In a preferred embodiment, the L-lactate is sodium L-lactate or potassium L-lactate.

In another embodiment, instead of having L-lactate in the perfusion medium, additional sodium bicarbonate is delivered to the fresh medium or to perfusion bioreactor when the pH of the perfusion culture goes above the predetermined value (i.e., pH 7 or a pH of 6.8-7.4). A typical cell culture medium contains about 1.0 to 2.5 g/L of sodium bicarbonate. In this embodiment, however, an additional 1 to 3 grams of sodium bicarbonate is added to the perfusion medium for every 1 liter of perfusion media added to the perfusion cell culture bioreactor when the pH of the cell culture is above pH 6.8 or above pH 7 or above pH 7.4 or above any pH within the range of 6.8 to 7.4. Once the pH drops below the predetermined value, the delivery of sodium bicarbonate is stopped or discontinued. Any other physiologically acceptable base (e.g., sodium carbonate, potassium carbonate, HEPES buffer, or the like), which is known to one of ordinary skill in the art, may be used in place of sodium bicarbonate so long as such base is added to the perfusion bioreactor slowly and at a rate that would provide an upward influence on the pH in a manner similar to that which would occur by the consumption of lactate from the perfusion medium as lactic acid. For example, instead of sodium bicarbonate being added to the perfusion medium, sodium carbonate can be added to the perfusion bioreactor slowly when the pH is above the predetermined value. In an exemplary embodiment, the sodium carbonate is added to the perfusion bioreactor such that 1 molar carbonate enters the perfusion bioreactor at a rate of 8.7 mL per 1 liter of perfusion medium utilized.

The fresh medium in this method requires at least glucose and amino acids. In an embodiment, the concentration of glucose is in the range of about 0.5 to about 40 g/L. In another embodiment, the fresh medium contains L-lactate. The concentration of L-lactate is in the range of about 0.1 and about 7.0 g/L. The ratio of moles of glucose to amino acids is between about 0.25 and 1.0. In another embodiment, the fresh medium further contains sodium bicarbonate, in addition to or in place of L-lactate, in an amount of about 2 to 5.5 g/L. In another embodiment, the fresh perfusion medium contains both L-lactate (in an amount of about 0.1 to 7 g/L) and sodium bicarbonate (in an amount of about 2 to about 5.5 g/L) such that the cells will be able to control their perfusion rate over the entire continuous perfusion period according to the subject technology.

Thus, in an aspect, the subject technology relates to a perfusion culture process, including: (a) monitoring pH in a cell culture in a perfusion bioreactor with a pH sensor; (b) delivering fresh medium and removing permeate when the pH is above a predetermined value; and (c) deactivating the medium delivery and the permeate removal when the pH is below the predetermined value. In one or more embodiments related, directly or indirectly, to this aspect to each other, the fresh medium includes L-lactate; the L-lactate is present in the fresh medium in an amount of about 0.1 g/L to 7.0 g/L; the L-lactate is present in the fresh medium in an amount of about 1 to 4 g/L; the L-lactate is present in the fresh medium in an amount of about 1 to 3 g/L; the L-lactate is present in the fresh medium in an amount of about 1 to 2.5 g/L; alternatively or in addition to L-lactate, additional sodium bicarbonate is added to the perfusion medium or the perfusion bioreactor in an amount of about 1 to about 2.5 g/L such that the total sodium bicarbonate in the culture medium is about 2 to about 5.5 g/L and wherein the additional sodium bicarbonate is delivered to the perfusion bioreactor when the pH is above the predetermined value; the additional sodium bicarbonate is added to the perfusion bioreactor such that 1 molar carbonate enters the perfusion bioreactor at a rate of 8.7 mL per 1 liter of perfusion medium utilized; alternatively or in addition to L-lactate, any other physiologically acceptable base such as sodium carbonate, potassium carbonate, or the like is added to the perfusion bioreactor in an amount that would provide an upward influence on the pH in a manner similar to that which would occur by the addition of L-lactate; the fresh medium includes: (a) glucose; (b) L-lactate and/or additional sodium bicarbonate; and (c) amino acids; the fresh medium includes: (a) between about 0.5 to about 40 g/L glucose; (b) between about 0.1 to about 7 g/L L-lactate and/or between about 2 to about 5.5 g/L sodium bicarbonate; and (c) amino acids in a mole-of-glucose-to-mole-of-amino-acids ratio of between about 0.25 to about 1.0; the fresh medium includes glucose in an amount equal to about 70 mM of amino acids and about 5.3 grams of glucose per liter of medium; the fresh medium includes glucose at an amino-acids-(in mM)-to-glucose-(in g/L) ratio selected from the group consisting of about 60 to about 4.2; about 90 to about 8; about 100 to about 12; about 120 to about 13; about 240 to about 42 and about 380 to about 70 per liter of medium; the predetermined pH value is about pH 7 or is about 6.8 to about 7.4; a measurement of glucose concentration in the cell culture or addition of glucose to the cell culture by a glucose pump is not required.

In another aspect, the subject technology relates to a method for achieving rapid cell growth in a perfusion culture process, comprising: (a) monitoring pH in a cell culture in a perfusion bioreactor with a pH sensor; (b) delivering fresh medium and removing permeate when the pH is above a predetermined value; and (c) deactivating the medium delivery and the permeate removal when the pH is below the predetermined value. In one or more embodiments related, directly or indirectly, to this aspect to each other, the fresh medium comprises L-lactate; L-lactate is in an amount of about 0.1 g/L to 7.0 g/L; alternatively or in addition to L-lactate, additional sodium bicarbonate is added to the perfusion bioreactor in an amount of about 1 to about 2.5 g/L such that the total sodium bicarbonate in the culture medium is about 2 to about 5.5 g/L and wherein the additional sodium bicarbonate is delivered to the perfusion bioreactor when the pH is above the predetermined value; the additional sodium bicarbonate is added to the perfusion bioreactor such that 1 molar carbonate enters the perfusion bioreactor at a rate of 8.7 mL per 1 liter of perfusion medium utilized; alternatively or in addition to L-lactate, any other physiologically acceptable base such as sodium carbonate, potassium carbonate, or the like is added to the perfusion bioreactor in an amount that would provide an upward influence on the pH in a manner similar to that which would occur by the addition of L-lactate; the fresh medium includes: (a) glucose; (b) L-lactate and/or additional sodium bicarbonate; and (c) amino acids; the fresh medium includes: (a) between about 0.5 to about 40 g/L glucose; (b) between about 0.1 to about 7 g/L L-lactate and/or between about 2 to about 5.5 g/L sodium bicarbonate; and (c) amino acids in a mole-of-glucose-to-mole-of-amino-acids ratio of between about 0.25 to about 1.0; the fresh medium includes glucose in an amount equal to about 70 mM of amino acids and about 5.3 grams of glucose per liter of medium; the fresh medium includes glucose at an amino-acids-(in mM)-to-glucose-(in g/L) ratio selected from the group consisting of about 60 to about 4.2; about 90 to about 8; about 100 to about 12; about 120 to about 13; about 240 to about 42 and about 380 to about 70 per liter of medium; the predetermined pH value is about pH 7 or is about 6.8 to about 7.4; a measurement of glucose concentration in the cell culture or addition of glucose to the cell culture by a glucose pump is not required; a viable cell density of about $60\times10^6$/mL is achieved within 4 days.

Another aspect of the subject technology relates to a hybrid perfusion/fed-batch culture process. This process comprising using the continuous perfusion process described above in combination with a fed-batch process. According to the subject technology, the process would run in perfusion mode for 4 to 6 days prior to being switched to fed-batch mode for an additional 4 to 8 days. By using this hybrid mode, volumetric productivity of equal to about or greater than 1.0 gram/L/day is achieved. In this embodiment, the continuous perfusion culture process includes steps (a) monitoring pH in a cell culture with a pH sensor; (b) delivering fresh medium and removing permeate when the pH is above a predetermined value; (c) and deactivating the medium delivery and the permeate removal when the pH is below the predetermined value.

Another aspect of the subject technology relates to a continuous perfusion bioreactor which consists of two significantly different phases. The first phase includes the initial continuous phase as mentioned above (ramp up of cell density and perfusion rate using HIPCOP) utilizing a comparably dilute medium, followed by a second phase of perfusion in which the perfusion rates are significantly reduced by utilization of a highly concentrated perfusion medium. By using this two-phase perfusion system, volumetric productivities of equal to about or greater than 1.5 grams/L/day is achieved while using very modest volumes of perfusion medium. No significant cell bleed (removal of cells from the bioreactor) occurs in the examples presented in this application.

Another aspect of the subject technology relates to the use of a diluent liquid that is added to the bioreactor during the later stages of the perfusion culture when the concentrated perfusion medium is being added to the bioreactor. In one embodiment, such a diluent liquid is a solution of saline of appropriate concentration. Because the long-distance transport of liquid nutrient medium can incur many difficulties (cost of transport, maintenance of sterility, temperature control) there is significant value in using highly concentrated perfusion medium in an industrial setting. Such medium allows for perfusion rates as low as 0.05-0.30 reactor volumes per day for the concentrated perfusion medium. In a related embodiment, in such a bioreactor system it is necessary to flush product material out of the bioreactor, particularly if a continuous downstream process is linked directly to capture the continuously delivered upstream harvest material (e.g., the material coming through the hollow fiber cell retention system), and if the protein being produced is highly labile.

In another aspect, the subject technology relates to a hybrid culture process, including a first continuous perfusion culture process followed by a second continuous perfusion culture process, wherein the first continuous perfusion culture process includes steps (a) monitoring pH in a cell culture with a pH sensor; (b) delivering fresh medium and removing permeate when the pH is above a predetermined value; (c) and deactivating the medium delivery and the permeate removal when the pH is below the predetermined value; and wherein the second continuous perfusion culture process includes steps of (a) adding a concentrated medium; and (b) adding a diluent. In a related embodiment, the hybrid culture process optionally includes an intervening fed-batch step. In this embodiment, the first continuous perfusion culture process is carried out first followed by a fed-batch step which is then followed by the second continuous perfusion culture process. In one or more embodiments related, directly or indirectly, to this aspect to each other, the continuous perfusion culture process is the first culture process; the continuous perfusion culture process is followed by a fed-batch process; the continuous perfusion culture process is followed by a second continuous perfusion culture process; the second continuous perfusion culture process comprises the steps of: (a) adding a concentrated medium; and (b) adding a diluent; the concentrated medium comprises 600 millimolar amino acids, 90 grams/liter glucose, 0 g/L sodium L-lactate; the diluent is selected from the group consisting of saline and water; the saline or water normalizes osmotic strength of culture medium to between about 0 to 250 and/or 250 to 350 mOsm/kg; the saline comprises 2.0 g/L sodium bicarbonate, 2.4 g/L polyvinyl alcohol, 20 mM potassium chloride, and 80 mM sodium chloride; the hybrid culture process results in volumetric productivity of greater than 1 gram cells/L/day; the hybrid culture process is performed in a culture volume of about 50 and about 150 L; the culture volume is about 70 L.

In another aspect, the subject technology relates to a bioreactor for conducting a continuous perfusion culture process, wherein the continuous perfusion culture process includes steps of: (a) monitoring pH in a cell culture in a perfusion bioreactor with a pH sensor; (b) delivering fresh medium and removing permeate when the pH is above a predetermined value; (c) and deactivating the medium delivery and the permeate removal when the pH is below the predetermined value. In one or more embodiments related, directly or indirectly, to this aspect to each other, the fresh medium comprises: (a) glucose; (b) L-lactate; and (c) amino acids; L-lactate is in an amount of about 0.1 g/L to 7.0 g/L; alternatively or in addition to L-lactate, additional sodium bicarbonate is added to the perfusion bioreactor in an amount of about 1 to about 2.5 g/L such that the total sodium bicarbonate in the culture medium is about 2 to about 5.5 g/L and wherein the additional sodium bicarbonate is delivered to the perfusion bioreactor when the pH is above the predetermined value; the additional sodium bicarbonate is added to the perfusion bioreactor such that 1 molar carbonate enters the perfusion bioreactor at a rate of 8.7 mL per 1 liter of perfusion medium utilized; alternatively or in addition to L-lactate, any other physiologically acceptable base such as sodium carbonate, potassium carbonate, or the like is added to the perfusion bioreactor in an amount that would provide an upward influence on the pH in a manner similar to that which would occur by the addition of L-lactate; the fresh medium includes: (a) glucose; (b) L-lactate and/or additional sodium bicarbonate; and (c) amino acids; the fresh medium includes: (a) between about 0.5 to about 40 g/L glucose; (b) between about 0.1 to about 7 g/L L-lactate and/or between about 2 to about 5.5 g/L sodium bicarbonate; and (c) amino acids in a mole-of-glucose-to-mole-of-amino-acids ratio of between about 0.25 to about 1.0; the fresh medium includes glucose in an amount equal to about 70 mM of amino acids and about 5.3 grams of glucose per liter of medium; the fresh medium includes glucose at an amino-acids-(in mM)-to-glucose-(in g/L) ratio selected from the group consisting of about 60 to about 4.2; about 90 to about 8; about 100 to about 12; about 120 to about 13; about 240 to about 42 and about 380 to about 70 per liter of medium; the predetermined pH value is about pH 7 or is about 6.8 to about 7.4; a measurement of glucose concentration in the cell culture or addition of glucose to the cell culture by a glucose pump is not required.

In another aspect, the subject technology relates to a protein of interest produced by a method including: (a) culturing cells comprising a gene that encodes the protein of interest in a perfusion cell culture bioreactor under conditions that allow production of the protein of interest including: (i) monitoring pH in the cell culture in a perfusion bioreactor with a pH sensor; (ii) delivering fresh medium and removing permeate when the pH is above a predetermined value; and (iii) deactivating the medium delivery and the permeate removal when the pH is below the predetermined value, (b) harvesting the protein of interest from the cell culture bioreactor. In one or more embodiments related, directly or indirectly, to this aspect to each other, the fresh medium includes: (a) glucose, (b) L-lactate, and (c) amino acids; L-lactate is in an amount of about 0.1 g/L to 7.0 g/L; alternatively or in addition to L-lactate, additional sodium bicarbonate is added to the perfusion bioreactor in an amount of about 1 to about 2.5 g/L such that the total sodium bicarbonate in the culture medium is about 2 to about 5.5 g/L and wherein the additional sodium bicarbonate is delivered to the perfusion bioreactor when the pH is above the predetermined value; the additional sodium bicarbonate is added to the perfusion bioreactor such that 1 molar carbonate enters the perfusion bioreactor at a rate of 8.7 mL per 1 liter of perfusion medium utilized; alternatively or in addition to L-lactate, any other physiologically acceptable base such as sodium carbonate, potassium carbonate, or the like is added to the perfusion bioreactor in an amount that would provide an upward influence on the pH in a manner similar to that which would occur by the addition of L-lactate; the fresh medium includes: (a) glucose; (b) L-lactate and/or additional sodium bicarbonate; and (c) amino acids; the fresh medium includes: (a) between about 0.5 to about 40 g/L glucose; (b) between about 0.1 to about 7 g/L L-lactate and/or between about 2 to about 5.5 g/L sodium bicarbonate; and (c) amino acids in a mole-of-glucose-to-mole-of-amino-acids ratio of between about 0.25 to about 1.0; the fresh medium includes glucose in an amount equal to about 70 mM of amino acids and about 5.3 grams of glucose per liter of medium; the fresh medium includes glucose at an amino-acids-(in mM)-to-glucose-(in g/L) ratio selected from the group consisting of about 60 to about 4.2; about 90 to about 8; about 100 to about 12; about 120 to about 13; about 240 to about 42 and about 380 to about 70 per liter of medium; the predetermined pH value is about pH 7 or is about 6.8 to about 7.4; a measurement of glucose concentration in the cell culture or addition of glucose to the cell culture by a glucose pump is not required.

BRIEF DESCRIPTION OF THE DRAWINGS

These and other features, aspects, and advantages of the claimed methods, apparatuses, and systems are better understood when the following detailed description is read with reference to the accompanying drawings:

FIG. 3 (A-E) illustrates the results of CHO cell line A growth in a 2 L bioreactor (as described in Example 1). Open symbols represent results when using the HIPCOP technology. Solid symbols represent the non-glucose limited condition. Perfusion is 'self-initiated' when the pH of the culture begins to rise as lactic acid is first removed from the bulk culture causing a rise in pH.

FIG. 4 (A-C) illustrates the results of CHO cell line B growth in a 2 L bioreactor using HIPCOP method of controlling perfusion rate (as described in Example 1).

FIG. 6 (A-E) illustrates the results of four different glutamine-sythetase expression system CHO cell lines (cell lines A, B, C, and D) producing IgG antibodies grown in 2 L bioreactors using the HIPCOP perfusion technology until day 4 and then converting to a fed-batch operational mode for the remainder of the 12-day culture.

FIG. 8 illustrates the modest volumes of perfusion medium (expressed in reactor volumes of perfusion medium) that are used during the HIPCOP phase of perfusion to achieve the high cell densities and productivities indicated in FIGS. 6A-E and FIG. 7. This table also shows the calculated maximum volumetric productivity which can be obtained from FIG. 7 by dividing by the number of days of culture at any time point in the culture.

In FIG. 9F the total perfusion rate is indicated by solid diamonds, the concentrated perfusion medium by solid squares, and the saline diluent by open squares.

FIG. 12 (A-C) illustrates the results of a DG-44 derived CHO cell line E producing a recombinant protein of ~130 kDa. Growth occurs in 3L bioreactor using HIPCOP method of controlling perfusion rate (as described in Example 1).

FIG. 13 (A-C) illustrates the results of a GS-CHO cell line B producing a recombinant immunoglobulin G. Growth occurs in 3 L bioreactor using HIPCOP method of controlling perfusion rate (as described in Example 1).

FIG. 14 (A-E) illustrates the results of a GS-CHO cell line B producing a recombinant immunoglobulin G. Culture was maintained in a 3 L bioreactor using HIPCOP method of controlling perfusion rate (as described in Example 1).

DETAILED DESCRIPTION OF THE SUBJECT TECHNOLOGY

Figure 1:
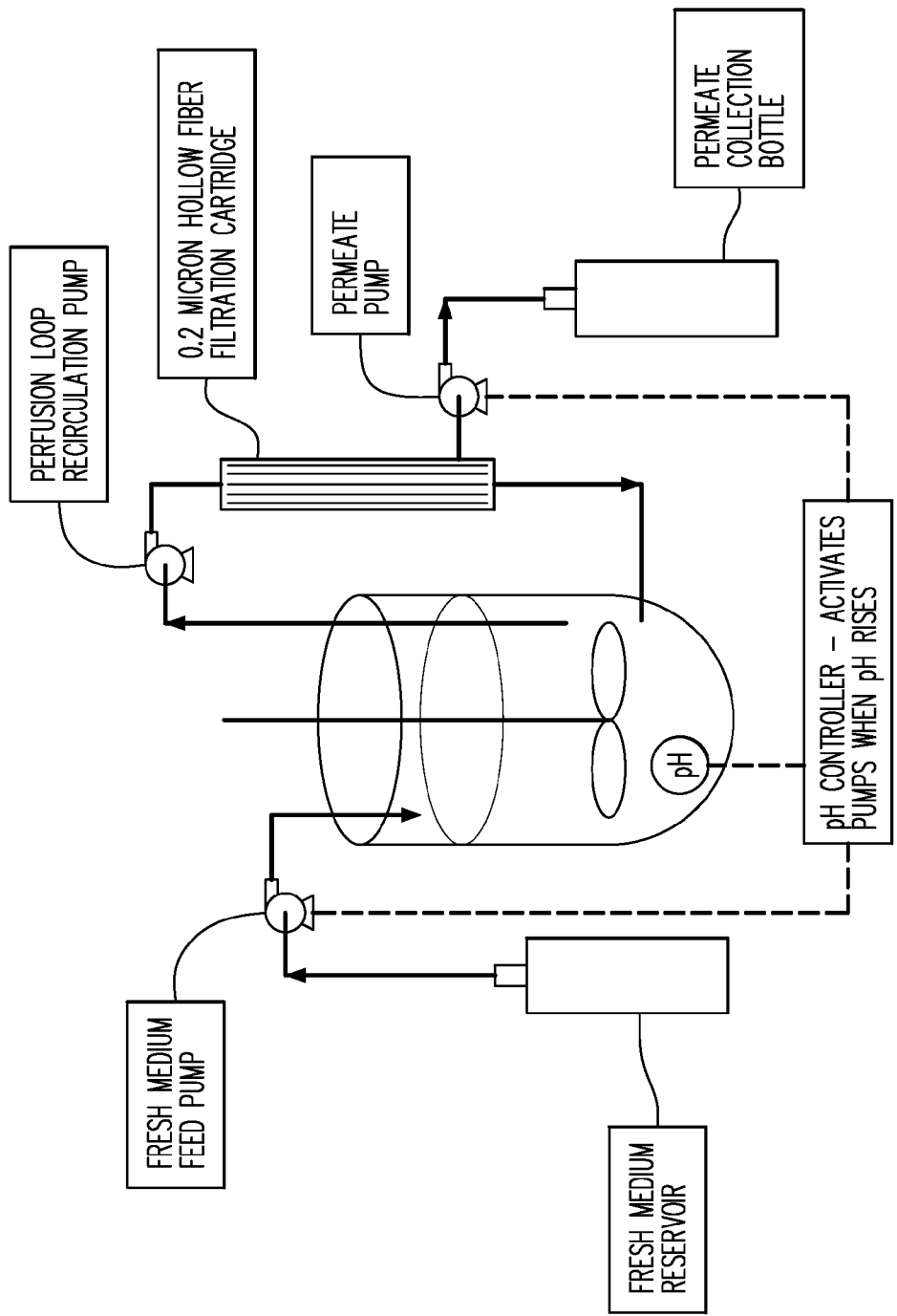
FIG. 1 shows a diagram of a perfusion apparatus.

The subject technology relates to methods for continuous perfusion culture by allowing cells to self-regulate the rate of addition of perfusion medium to the bioreactor via a pH change and where the perfusion medium comprises glucose, L-lactate (and/or sodium bicarbonate) and a specified ratio of amino acids to glucose. Advantages of this technology include increased protein production while optimizing process conditions such as using less liquid media.

The subject technology is, in part, based on the surprising discovery that L-lactate, a potentially growth inhibiting compound, can advantageously be added to the perfusion medium for cells to be able to control their perfusion rate over the entire continuous perfusion period.

Definitions

The term "about" generally refers to a slight error in a measurement, often stated as a range of values that contain the true value within a certain confidence level (usually ±1 σ for 68% C.I.). The term "about" may also be described as an integer and values of ±20% of the integer.

The term "about pH 7" refers to pH 7±1 pH units. In an embodiment, the about pH 7 refers to pH 7±0.2 pH units. In another embodiment, the about pH 7 refers to pH of 6.8 to 7.4. In another embodiment, the about pH 7 refers to pH 7.10±0.025 pH units. For example, the pH setpoint (or predetermined value) and deadband during perfusion may be set to 7.10±0.025. At this value, the perfusion pump is triggered at the high-end of this range, e.g., a pH of 7.125. When the pH rises above 7.125, the perfusion pump will turn on, and when the pH drops below 7.125, the pump will turn off. A separate pump may be activated to add an alkaline solution when the pH drops below the low-end of the range at 7.075.

Lactic acid or 2-hydroxypropanoic acid ($CH_3CHOHCOOH$) is an organic acid produced and consumed by certain cells during culture. Lactic acid is chiral and has two optical isomers. One is known as L-(+)-lactic acid (chiral, (S)-lactic acid) and the other, its mirror image, is D-(⁻)-lactic acid (chiral, (R)-lactic acid). A mixture of the two in equal amounts is called DL-lactic acid.

L-lactate refers to an ester or salt of lactic acid. Lactate is a by-product of culture and is produced during cellular respiration as glucose is broken down. Esters of lactic acid may include, but are not limited to, methyl L-lactate, ethyl L-lactate, butyl L-lactate, ethylhexyl L-lactate, lauryl L-lactate, myristyl L-lactate, or cetyl L-lactates. Salts of L-lactates may refer to alkali metal L-lactates such as potassium L-lactate, sodium L-lactate, lithium L-lactate, or ammonium L-lactate, as well as alkali earth metal L-lactates such as calcium L-lactate, magnesium L-lactate, strontium L-lactate, or barium L-lactates. In addition, L-lactates of other divalent, trivalent and tetravalent metals may include zinc L-lactate, aluminum L-lactate, iron L-lactate, chromium L-lactate, or titanium L-lactate. In accordance with this subject technology, any ester or salt of lactic acid may be used.

The term "volumetric productivity" refers to the amount of material produced per volume per time of run. For mammalian cell culture, this value may be reported as grams/L/day.

The term "permeate" refers to the liquid (including the spent medium and the expressed protein) that leaves the bioreactor through one or more filters, membranes or other cell retention devices. Depending on the type of the filter/membrane or other cell retention device it passes through, permeate may be cell-free or may contain a residual amount of cells.

Continuous Perfusion

During continuous perfusion culture of mammalian cells, medium is perfused through a culture while the cell mass is contained within the bioreactor by means of a cell retention device (FIG. 1). In a suspension culture system, the cell retention device is commonly a filter of some type, but numerous other methods can be employed (sonic separation, inclined plane settling, external centrifuges, internal filters such as spinning or oscillating, external hydrocyclones, etc.) including some devices that might not be completely 'cell free'. As the cell mass continues to grow and increase in number and mass, the rate of perfusion increases to remove metabolic byproducts and supply necessary nutrients. The perfusion rate is commonly increased step-wise and in many cases, is determined based on a calculation in which a specific ratio of perfusion medium volume per time to cell number is maintained (CSPR, or cell-specific perfusion rate, often in nanoliters/cell/day, usually in the 0.05-0.5 nL/cell/day range). See Ozturk, Cytotechnology, 1996; 2: 3-16 and Konstantinov et al., Adv. Biochem. Eng/Biotechnol., 2006; 101: 75-98. In some instances, the perfusion rate is set to control the concentration of glucose or L-lactate (Konstantinov et al., Biotechnol. Prog, 1996; January-February; 12(1): 100-9 and Ozturk et al., Biotechnol. Bioeng., 1997; Feb. 20; 53(4): 372-8), or is based on oxygen uptake rate measurements. See Feng et al., J. Biotechnol., 2006; Apr. 20; 122(4): 422-430.

When compared with a fed-batch culture producing a similar amount of product protein, continuous perfusion cultures typically utilize much larger volumes of cell culture medium. The larger volumes of medium are not primarily needed to supply nutrients because the nutrient feeds can be highly concentrated and added in small volumes as in a fed-batch culture. The larger volumes of medium used in perfusion culture are typically employed to wash away metabolic byproducts of the cells. Cells in a perfusion culture typically undergo higher levels of shear and other environmental insults that require at least some growth of cells to make up for those that die. In addition, continuous cultures are expected to operate for significantly longer lengths of time, several weeks or even months, compared with a fed-batch culture that might last at most 10-18 days. Consequently, cells in a continuous culture should be maintained in a state that allows for at least some cell division. That state requires that the inhibitory metabolic byproducts are kept below a certain level.

The primary inhibitory compound generated by mammalian cells is lactic acid. This is particularly true when cells grow quickly. The lactic acid suppresses pH and requires that base titrant be added so that the pH can remain in a range appropriate for cell growth. The lactic acid is neutralized to L-lactate and the ion sodium (or potassium) enters the culture in large amounts as the typical counter ion for the high pH titrant. The L-lactate ion is itself inhibitory to growth at sufficiently high levels, but also the mere presence of the L-lactate and additional sodium ions significantly elevate the osmotic strength of the medium until it is outside of the normal physiological range of 280-320 mOsm (see Gagnon et al., Biotechnol. Bioeng., 2011; 108: 1328-1337). At a sufficiently high osmotic strength cell growth will slow and eventually productivity of a culture will also decrease.

Conventional continuous perfusion cultures often ramp up the perfusion rate in order to flush out accumulated L-lactate and keep cells growing at the start of a culture. This perfusion ramp up consumes large volumes of medium that might not otherwise be required if no L-lactate were produced.

Figure 2A:
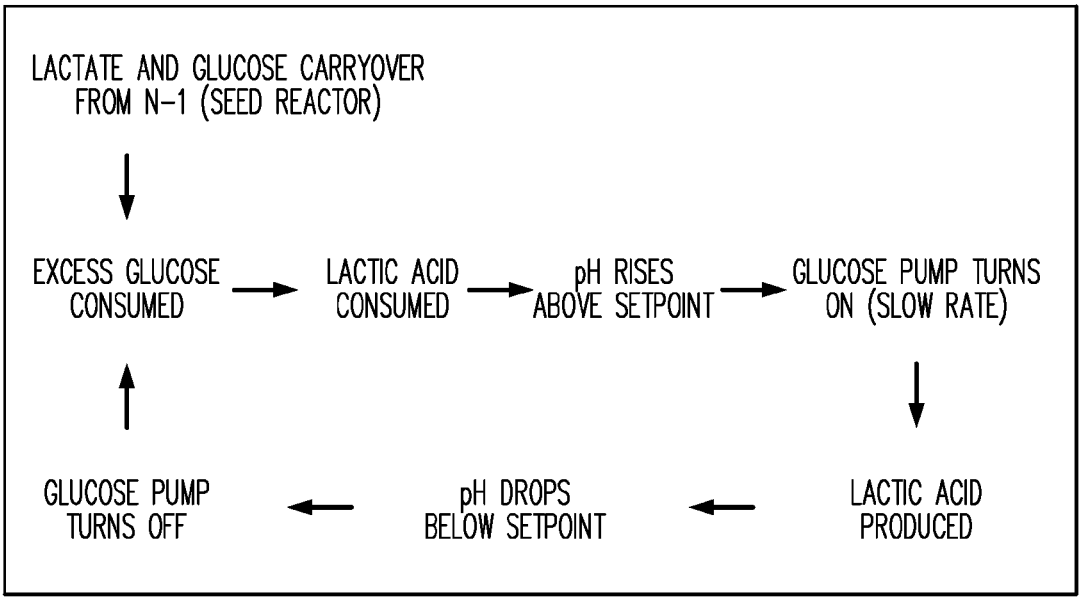
FIG. 2A illustrates a pictorial representation of hypothesized sequence of events occurring in the bulk cell culture fluid during the growth phase of a bioreactor utilizing the HIPDOG control scheme for limiting lactic acid accumulation in fed-batch culture.
Figure 2B:
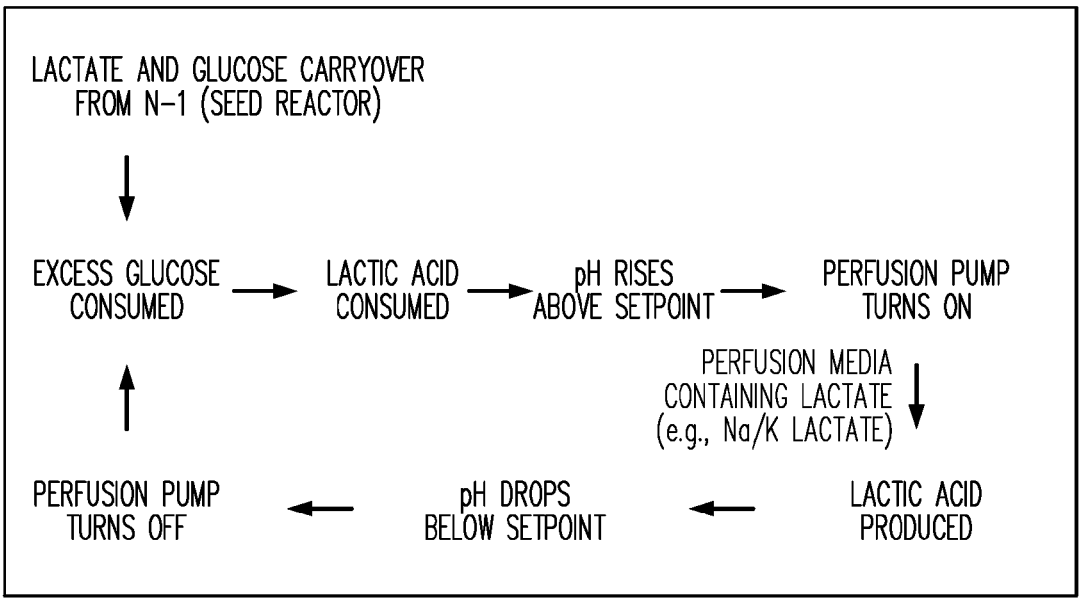
FIG. 2B illustrates a pictorial representation of hypothesized sequence of events occurring in the bulk cell culture fluid during the growth phase of a bioreactor utilizing the HIPCOP control scheme for cell-controlled perfusion rate ramp up in continuous perfusion culture.

When mammalian cells in culture are exposed to freely available glucose (concentrations perhaps above 2 mM) they typically produce high levels of lactic acid and continue to maintain high glucose consumption rates. However, when the glucose levels are low (below 2 mM), mammalian cells will cease the production of lactic acid and instead, will transport lactic acid from the bulk medium back across their membranes for consumption. The net uptake of lactic acid from the bulk fluid causes the pH of the culture to rise quickly. If the rise in pH triggers the slow addition of glucose to the culture, e.g., from a pump delivering a nutrient solution containing glucose, then the pH on the high end can be controlled to a near constant value at the same time as glucose (and potentially other nutrients) is delivered to the culture, resulting in the accumulation of lactic acid and its detrimental effects to the culture being suppressed. This process is the basis of previously described high-end pH delivery of glucose (HIPDOG) in FIG. 2A (Gagnon et al., Biotechnol. Bioeng., 2011; 108: 1328-1337, disclosing an experiment with a fed-batch culture). High-end pH-controlled delivery of glucose effectively suppresses L-lactate accumulation, for example, in CHO fed-batch cultures. The HIPDOG process may be described as cells self-determining their rate of glucose consumption because the cells indicate a need for additional glucose by taking up lactic acid and triggering a rise in the pH.

The HIPDOG fed-batch process may be extended to continuous perfusion culture of mammalian or CHO cells in the following manner. When glucose concentrations get too low in a continuous culture, the cells take up lactic acid, triggering a rise in pH. In a fed-batch culture a pump delivering a highly concentrated glucose solution is activated, i.e., the glucose concentration of the feed commonly being between about 50 and 500 g/L, whereas in continuous perfusion culture a pump may be activated to deliver a perfusion medium containing a lower concentration of glucose, for example between about 4 and 40 g/L glucose. In continuous perfusion culture the volume of the bioreactor is maintained constant. Therefore, any addition of perfusion medium coincides with an equivalent volume removal of culture medium from the bioreactor. This can be accomplished, for example, by using a laboratory balance which signals a pump to remove permeate whenever the weight of the bioreactor exceeds the tare weight. When the glucose level in the culture becomes non-limiting, the cells again excrete lactic acid which suppresses the bulk culture pH and deactivates the feed and permeate pumps that deliver and remove medium, respectively, to the culture. This cycle repeats again and again as the cells grow and metabolize. As the cell density of the culture increases, the cells are able to trigger the perfusion pump to turn on more and more frequently, thereby ramping up their rate of perfusion without any manual intervention.

During the above-described process, it was observed that the levels of L-lactate in the bulk culture fluid dropped over time. As a result, it was necessary in some cases to supplement the perfusion medium with sodium L-lactate, for example, between about 1 to 7 grams/L so that the control strategy did not break down.

Additional considerations regarding choosing the levels of nutrients and glucose in the perfusion medium were necessary. For example, during the early phases of the culture it was advantageous to quickly expand the cell mass and thus, maintain high growth rates. To keep growth rates high, comparatively high rates of perfusion were required to remove growth inhibitors other than L-lactate.

According to this subject technology, Hi-end pH Control of Perfusion or HIPCOP allowed the cells to determine their rate of perfusion which ultimately depended upon their rate of glucose consumption. At any one point in time, the volume of perfusion medium being delivered to the culture was dependent upon the glucose concentration in the perfusion medium. A higher concentration of glucose in the perfusion medium corresponds to a lower volume of perfusion medium being delivered. For this reason, there is value in having a lower concentration of glucose in the perfusion medium when high perfusion rates are preferred, and a high concentration of glucose in the perfusion medium when lower rates of perfusion are preferred. Since many operational parameters (oxygen transfer, carbon dioxide removal, etc.) limit the final peak viable cell densities that can practically be maintained in a large-scale perfusion bioreactor, there may be value in restricting cell growth after the initial expansion phase. When restricting additional cell division is desirable, it may be useful to utilize a perfusion medium with a higher concentration of glucose which would slow the perfusion rate and allow higher levels of inhibitory molecules to accumulate in culture.

According to this subject technology, glucose concentration used in the basal medium into which the cells are first inoculated is important. If the initial glucose level is too high, it is possible the cells might generate too much lactate early on in culture which would slow growth before perfusion could begin. With CHO cell culture, for example, initial glucose concentrations between about 2 to 4 grams/L range may be used with this subject technology.

Another consideration regarding the present subject technology is the importance of the ratio of glucose to other nutrients (principally amino acids) in the perfusion medium. To sustain cell growth and/or recombinant protein production rates, this ratio must be balanced such that the quantity of amino acids delivered to the culture is neither too high nor too low. It is possible that a different ratio of glucose to amino acids, likely lower, is necessary when cell biomass production is slower. Alternatively, a concentrated slow feed of pure amino acids or pure glucose could compensate for inaccurate approximations of the proper ratio of glucose to amino acids in the perfusion medium. If a pure glucose addition is necessary, this addition may need to be tied to the pH controller/sensor in an identical manner as the perfusion medium pump.

Thus, in an aspect, the subject technology relates to a perfusion culture process, including: (a) monitoring pH in a cell culture in a perfusion bioreactor with a pH sensor; (b) delivering fresh medium and removing permeate when the pH is above a predetermined value; and (c) deactivating the medium delivery and the permeate removal when the pH is below the predetermined value. In one or more embodiments related, directly or indirectly, to this aspect to each other, the fresh medium includes L-lactate; the L-lactate is present in the fresh medium in an amount of about 0.1 g/L to 7.0 g/L; the L-lactate is present in the fresh medium in an amount of about 1 to 4 g/L; the L-lactate is present in the fresh medium in an amount of about 1 to 3 g/L; the L-lactate is present in the fresh medium in an amount of about 1 to 2.5 g/L; alternatively or in addition to L-lactate, additional sodium bicarbonate is added to the perfusion bioreactor in an amount of about 1 to about 2.5 g/L such that the total sodium bicarbonate in the culture medium is about 2 to about 5.5 g/L and wherein the additional sodium bicarbonate is delivered to the perfusion bioreactor when the pH is above the predetermined value; the additional sodium bicarbonate is added to the perfusion bioreactor such that 1 molar carbonate enters the perfusion bioreactor at a rate of 8.7 mL per 1 liter of perfusion medium utilized; alternatively or in addition to L-lactate, any other physiologically acceptable base such as sodium carbonate, potassium carbonate, or the like is added to the perfusion bioreactor in an amount that would provide an upward influence on the pH in a manner similar to that which would occur by the addition of L-lactate; the fresh medium includes: (a) glucose; (b) L-lactate and/or additional sodium bicarbonate; and (c) amino acids; the fresh medium includes: (a) between about 0.5 to about 40 g/L glucose; (b) between about 0.1 to about 7 g/L L-lactate and/or between about 2 to about 5.5 g/L sodium bicarbonate; and (c) amino acids in a mole-of-glucose-to-mole-of-amino-acids ratio of between about 0.25 to about 1.0; the fresh medium includes glucose in an amount equal to about 70 mM of amino acids and about 5.3 grams of glucose per liter of medium; the fresh medium includes glucose at an amino-acids-(in mM)-to-glucose-(in g/L) ratio selected from the group consisting of about 60 to about 4.2; about 90 to about 8; about 100 to about 12; about 120 to about 13; about 240 to about 42 and about 380 to about 70 per liter of medium; the predetermined pH value is about pH 7 or is about 6.8 to about 7.4; a measurement of glucose concentration in the cell culture or addition of glucose to the cell culture by a glucose pump is not required.

In an embodiment, during the growth phase, a perfusion medium with a ratio of 70 mM of amino acids to 5.3 grams of glucose per liter or 60:4.2, respectively, is used. In conditions of slower growth, ratios of 90:8, 100:12, 120:13, 240:42 and 380:70 (mM amino acids:grams/L glucose) is used.

The subject technology's 'cell-controlled' perfusion system has significant advantages including decreasing the volumes of perfusion medium required, reducing the burden on cell retention systems, e.g., less filter area, small device size, more efficient separations at lower flow rates, etc., minimizing or eliminating the accumulation of the sodium and lactate ions in the culture, and minimizing osmotic strength increases. The improved culture conditions additionally allow for faster cell growth rates that are closer to maximum growth rates. The low osmotic strength and low levels of lactate is particularly valuable if the culture is to be transitioned in the final steps to a fed-batch culture where there is no simple method for the reduction of accumulated ions. The cell-controlled aspect of the subject technology means that the cells will 'self-start' the perfusion as well as self-control the rate of perfusion ramp up. Such 'cell-controlled' perfusion may allow for near instantaneous minor corrections in perfusion rate that is desirable due to minor perturbations in the environment of the culture. In many conventional perfusion bioreactors the perfusion rate is increased based upon a cell density being reached or an inhibitory metabolite reaching a pre-determined concentration. The need for sampling of the bioreactor might be reduced in a HIPCOP controlled perfusion system as the perfusion rate is controlled continuously by the rise in pH near instantaneously signaled by the cell metabolism. This opportunity to self-correct is particularly useful if the HIPCOP control is to be used for a long-duration continuous perfusion culture. Additionally, such a 'cell-controlled perfusion rate' process requires less time for process development as the optimal perfusion rates for delivery of glucose will be determined by the cells themselves.

Alternatively or in addition, the HIPCOP or 'cell-controlled perfusion rate' process of the subject technology relies on little or no glucose measurements, which lowers the dependency of the culture process on such values and thus simplifies the process to a large extent. Moreover, the HIPCOP process of the subject technology does not include a pump for delivering highly concentrated glucose solution to the bioreactor. In addition, the HIPCOP process uses smaller volumes of perfusion medium (generally less than 2 reactor volumes total during the cell expansion phase) than a typical conventional perfusion processes, which makes the process more advantageous over the conventional processes.

Thus, in an embodiment, the subject technology relates to HIPCOP or cell-controlled perfusion culture process which includes steps of (a) monitoring pH in a cell culture with a pH sensor; (b) delivering fresh medium and removing permeate when the pH is above a predetermined value; (c) and deactivating the medium delivery and the permeate removal when the pH is below the predetermined value. This process is different from, for example, monitoring pH in a cell culture with a pH sensor; delivering a fresh medium and removing permeate when the pH is below a predetermined value; and deactivating the medium delivery and the permeate removal when the pH is above the predetermined value. The latter process is based on the notion that if large amounts of lactic acid are being produced and the pH falls, the perfusion pumps are turned on. If the incoming medium is of high pH, the addition of medium will indeed push the pH of the culture higher, but it will also add an excess of glucose, trigger more lactate production, continuing in a 'vicious cycle' that will end up using large amounts of perfusion medium to flush out lactate. The HIPCOP process of the subject technology does not have these limitations.

The present subject technology could also be utilized for an N−1 (or seed) bioreactor in which perfusion is used to increase the cell density to provide a high-cell density inoculum of optimum health to the production bioreactor. The present subject technology could also be used for a production reactor either as part of a continuous perfusion culture, or during a short time span of perfusion (in the production reactor) prior to conversion to a conventional fed-batch mode of operation.

It is advantageous to expand cells quickly to very high density using a short duration of perfusion (continuous culture with cell retention), and then complete the production culture as a simple fed-batch bioreactor. The perfusion operation of such a culture would likely continuously 'ramp up' the perfusion rate as the cell density increased to keep the cells growing at a near exponential rate. While continuing to add complexity, there is also value in performing a short duration of perfusion with a dilute medium (which will add nutrients and remove waste products simultaneously) followed by perfusion at much lower rates with a highly concentrated medium (no longer efficiently flushing out inhibitors, but still adding sufficient nutrients to support production of the product of interest). Such a culture would allow for very fast growth to high density, and then allow for high productivity, and generally minimize the length of the culture such that it is of similar length to a more conventional fed-batch culture.

Thus, for a hybrid perfusion/fed-batch culture process, the process may be carried out in the following manner (numbers used for this example are taken from the process data presented from cell line A as in FIG. 6-8). Upon production bioreactor inoculation, a batch comprising a high inoculation density of approximately $5 \times 10^6$ cells/mL is cultured in an initial medium of 4 g/L glucose. After one day and for the following 3 days, the batch is switched to a continuous perfusion process where cells "self-control" the perfusion ramp up. Approximately 2.5 g/L sodium L-lactate is present in the perfusion medium. Perfusion occurs with approximately 60 L of working volume of which approximately 160 L total of perfusion medium is required. After three days, the process is switched to a standard fed-batch process and feeds continue until the bioreactor reaches 100 L on the day 12 of the culture. By using this hybrid perfusion/fed-batch culture process, volumetric productivity of equal to or greater than 1 gram cells/L/day has been achieved. Additionally, if a typical conventional perfusion ramp up was used, it is likely that 2-3 times more perfusion medium would have been required and additional filter area for the cell retention system may have also been required to achieve similar results.

In an embodiment relating to the hybrid perfusion/fed-batch culture process, the perfusion process is implemented first for the cell culture and the fed batch process is implemented second. In another related embodiment, the perfusion process starts first and lasts for 1 to 12 days and the fed-batch process follows the perfusion process and lasts for additional 1 to 12 days. In an exemplary embodiment, the perfusion process lasts for 3 to 5 days (typically starting automatically within 24 hours of inoculation) and the fed-batch process follows the perfusion process and lasts for additional 9 to 11 days. The advantages of this hybrid system are very high volumetric productivity, fits in standard fed-batch window, and fits in existing facilities (e.g., single harvest). The HIPCOP in this system allows cells to control their own perfusion rates; it adjusts to minor process deviations and lactate, ammonia, osmolality remain very low just prior to start of fed-batch.

Another embodiment of the subject technology relates to a continuous perfusion bioreactor which consists of two significantly different phases. The first phase includes the initial continuous phase as mentioned above (ramp up of cell density and perfusion rate using HIPCOP) utilizing a comparably dilute medium, followed by a second phase of perfusion in which the perfusion rates are significantly reduced by utilization of a highly concentrated perfusion medium.

Another embodiment of the subject technology relates to the use of a diluent liquid that is added to the bioreactor during the later stages of the perfusion culture when the concentrated perfusion medium is being added to the bioreactor. In one embodiment, such a diluent liquid is a solution of saline of appropriate concentration (e.g., 2.0 g/L sodium bicarbonate, 2.4 g/L polyvinyl alcohol, 20 mM potassium chloride, and 80 mM sodium chloride). Because the long-distance transport of liquid nutrient medium can incur many difficulties (cost of transport, maintenance of sterility, temperature control) there is significant value in using highly concentrated perfusion medium in an industrial setting. Such medium allows for perfusion rates as low as 0.05-0.30 reactor volumes per day for the concentrated perfusion medium. In a related embodiment, in such a bioreactor system it necessary to flush product material out of the bioreactor, particularly if a continuous downstream process is linked directly to capture the continuously delivered upstream harvest material, and if the protein being produced is highly labile. Additionally, in order to avoid an excessively large downstream it may also be advantageous to control the mass per day of product entering the downstream process within a small range. This can also be facilitated by manipulating the flow rate of the diluent, e.g., saline. It is also advantageous to maintain the osmotic strength of the bioreactor environment close to the physiological range of 250-350 mOsm. Cells often produce extraneous metabolites that increase the osmotic strength of the culture and can negatively impact culture health and cellular productivity.

Additionally, since the perfusion medium in the late stage of the continuous culture is extremely concentrated and there may be variability of cellular uptake rates of amino acids, some amino acids might accumulate in the bioreactor, potentially also negatively impacting the culture environment due to toxicity or merely due to their contribution to the increase in osmotic strength. Both of these objectives (flushing product material or accumulating unconsumed nutrients out of the bioreactor, and maintaining appropriate culture osmotic strength) might be facilitated by a feed to the bioreactor of a solution of saline at the optimal concentration (e.g., between about 250 to 350 mOsm/kg or between about 0 to 250 mOsm/kg). Such a diluent could be continuously added to the bioreactor and its saline content could be continuously adjusted by addition of sterile water (again with the goal of potentially minimizing the need to transport/ship large volumes of liquid) such that the near optimal culture environment could be maintained at any time point of the culture. Feed-back control using in-line or off-line analysis of osmotic strength and product concentration could also facilitate the addition of the proper amount and concentration of the salt and water solutions. Furthermore, the saline or diluent solution could be near saturation with sodium chloride, or more preferentially have a mixture of sodium chloride and potassium chloride near saturation so that additional potassium can be supplied as a nutrient to the culture, or that a more physiologically appropriate ratio of potassium to sodium ion might be maintained in the culture.

EXAMPLES

Example 1

The Application of HIPCOP Technology at the 1-2 Liter Scale

Figure 3A:
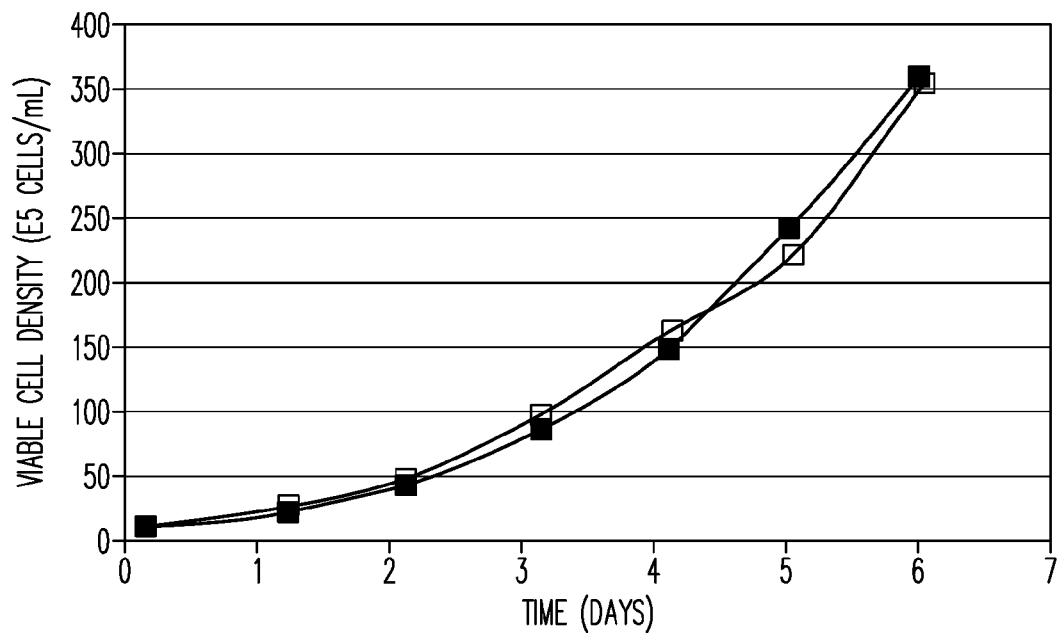
FIG. 3A shows viable cell density (E5 cells/mL) over time (days)
Figure 3B:
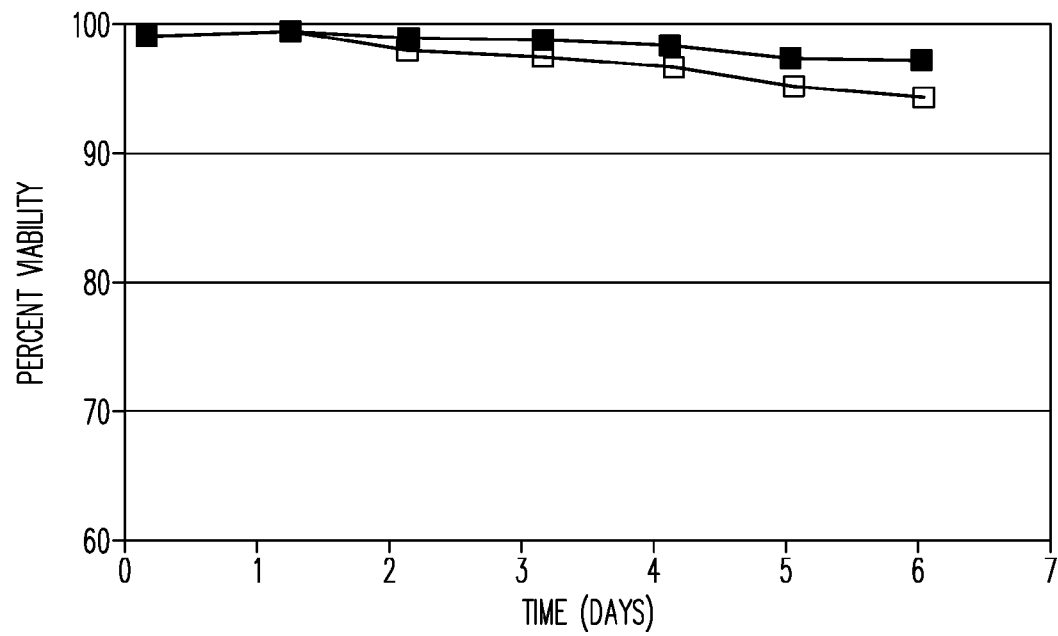
FIG. 3B shows viability (%) over time (days)
Figure 3C:
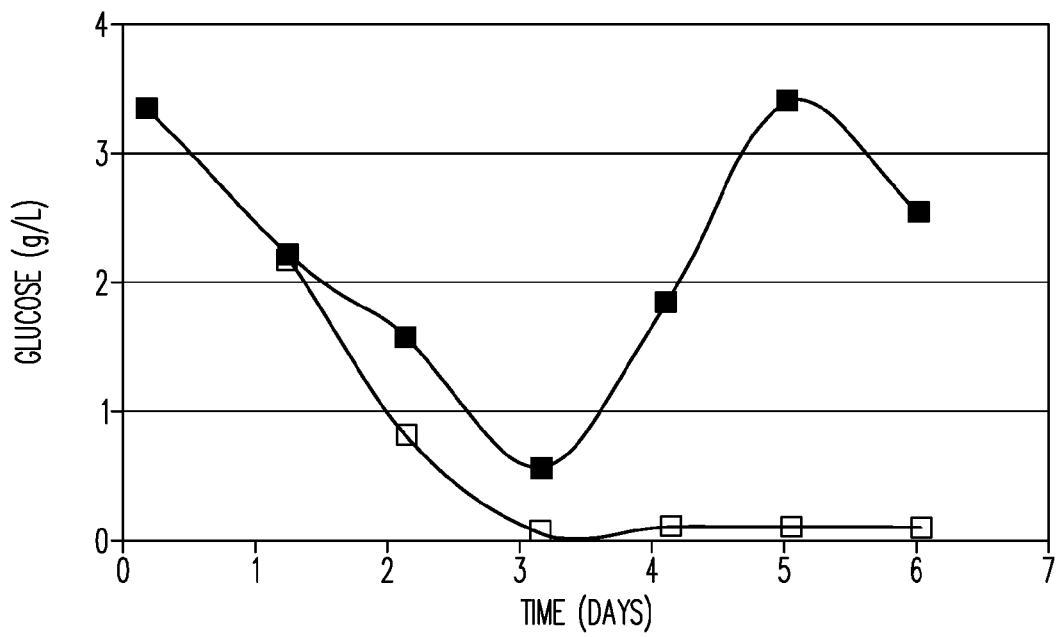
FIG. 3C shows glucose (g/L) over time (days)
Figure 3D:
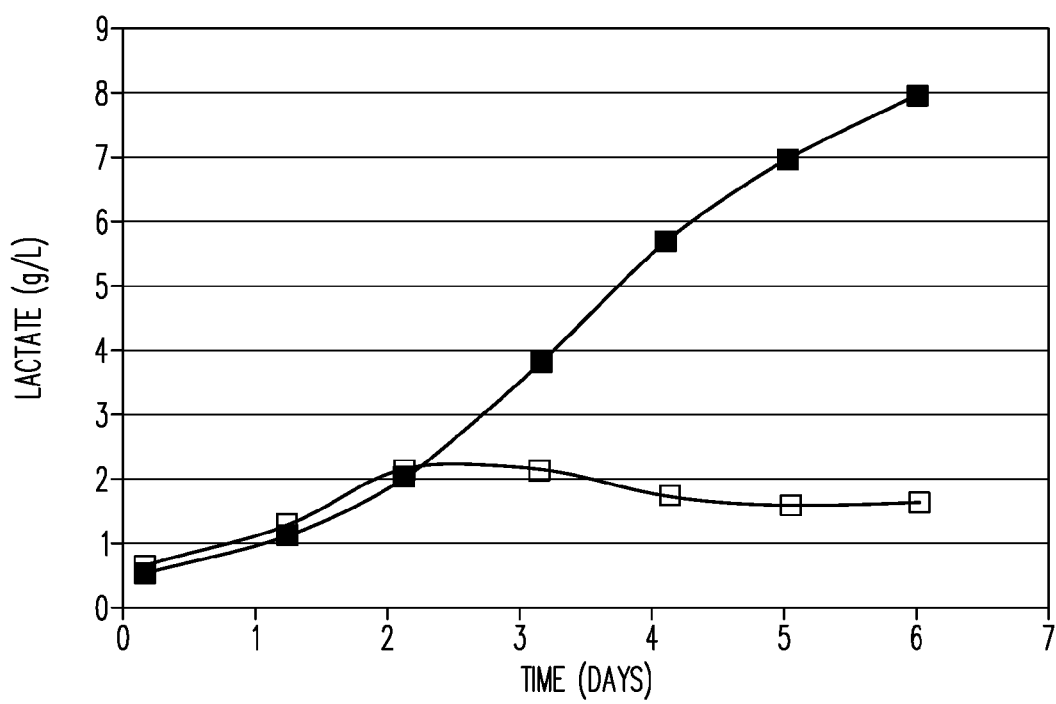
FIG. 3D shows L-lactate concentration (g/L) over time (days)
Figure 3E:
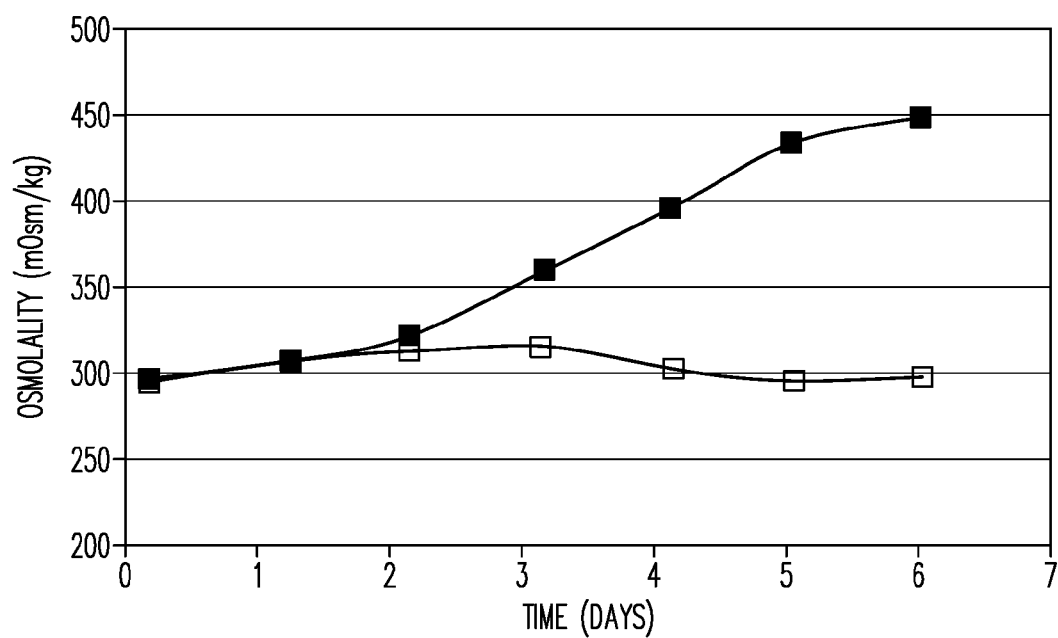
FIG. 3E shows osmolality (mOsm/kg) over time (days).

Multiple tests using HIPCOP (high-end pH control of perfusion) have been performed. This process was advantageous during the ramp up of perfusion as cell density increased. L-lactate was kept low and osmotic strength was maintained in an optimal range. FIGS. 3A-E compare two continuous perfusion cultures, one using HIPCOP and one maintained under non-limiting glucose conditions, i.e., additional glucose was added to the culture to maintain between about 0.5-3.5 g/L glucose. Both cultures had identical set points and dead bands for pH, dissolved oxygen, and temperature control. Perfusion started automatically between days 2 and 3 when the glucose in the HIPCOP bioreactor fell to a low level, lactic acid was taken up by the cells, and the bulk pH rose to trigger the startup of the perfusion medium addition and permeate removal pumps. The rate of addition of perfusion medium to the two cultures was identical, and was ramped up at the same rate controlled by the otherwise identical HIPCOP culture. The rate of cell growth was nearly identical in the two cultures despite the fact that the HIPCOP bioreactor maintained a nearly zero glucose concentration while the perfusion was occurring. Cell viabilities were also similar but slightly lower for the HIPCOP condition (FIG. 3B).

Because the non-limited glucose condition produced an excess of lactic acid and basic titrant was automatically added to maintain pH, a slightly higher overall volume of fluid (9% by volume more fluid) was passing through the cell mass when compared with the HIPCOP condition. While the cell densities and growth rates were very similar, far more L-lactate was produced in the non-limited glucose culture, and a far higher osmotic strength was reached as the culture progressed (see FIGS. 3D and 3E).

Figure 4A:
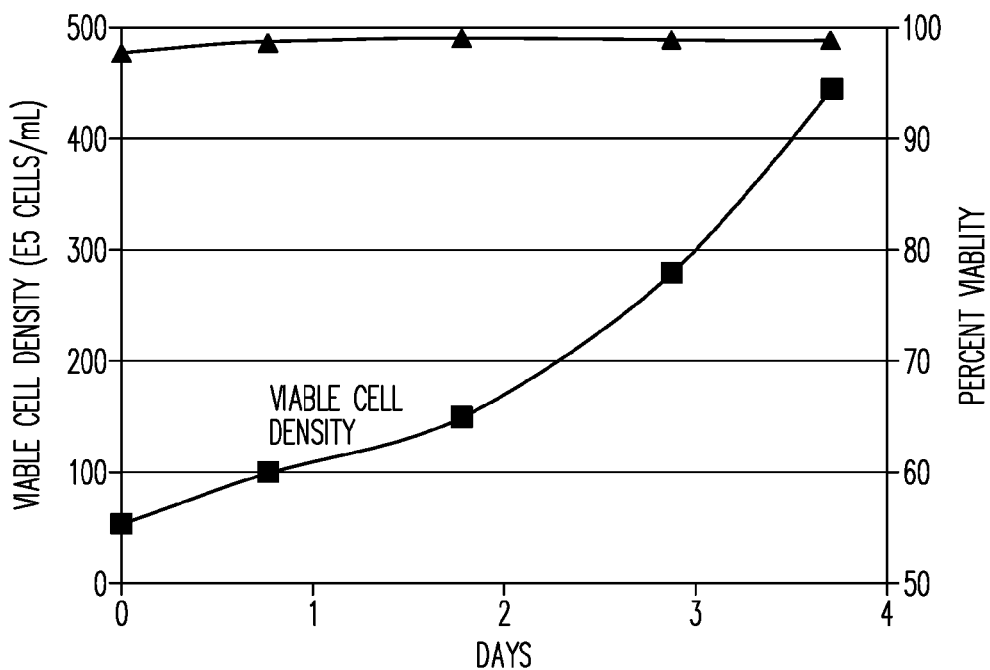
FIG. 4A shows either viable cell density (E5 cells/mL) or viability (%) over time (days)
Figure 4B:
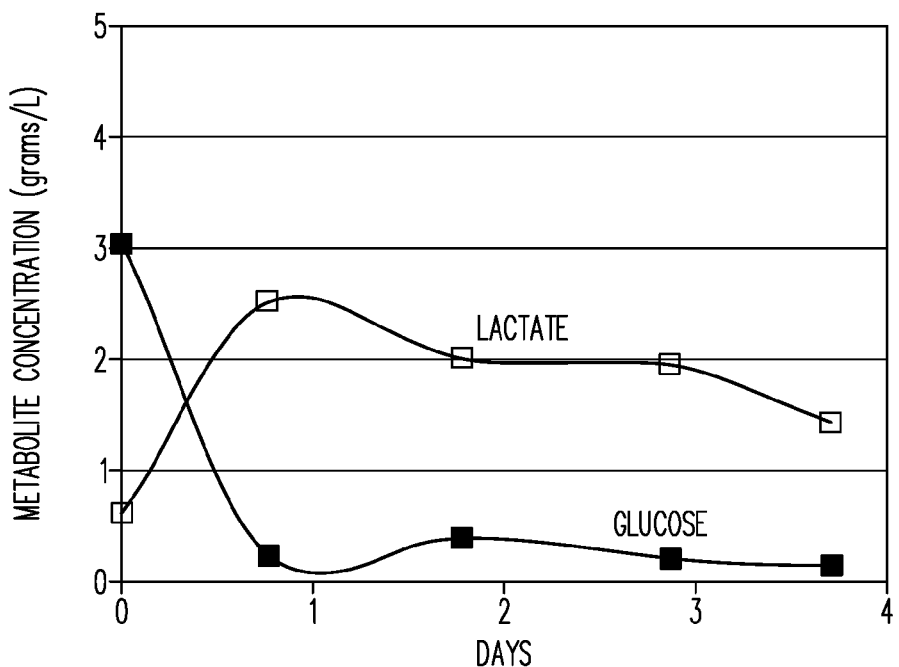
FIG. 4B shows metabolite concentration (g/L) over time (days)
Figure 4C:
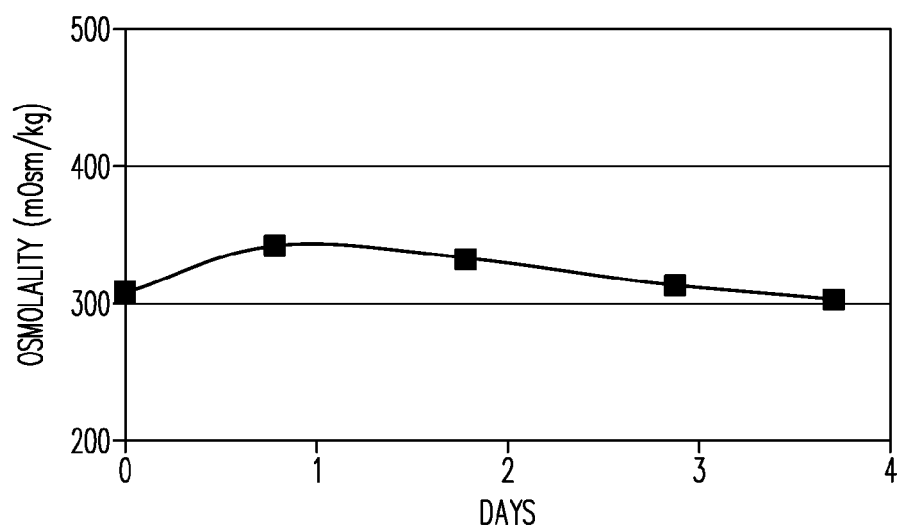
FIG. 4C shows osmolality (mOsm/kg) over time (days).

FIGS. 4A-C demonstrates the application of the HIPCOP technology to another CHO cell line (cell line B). Again the cells divided at a growth rate near the maximum growth rate for the CHO cell line. Again the L-lactate and osmotic strength of the culture was suppressed and the culture environment was near optimum for continued operation.

A specific example of fresh perfusion medium that may be used according to this subject technology comprises 8 g/L glucose, 2.5 g/L sodium L-lactate (i.e., 22 mM L-lactate ion) and 90 mM amino acids.

Example 2

The Application of HIPCOP Technology at the 70 Liter Scale

The following data shows that the technique of HIPCOP can easily be implemented at the 70-liter scale with similar results to that of the 1-2 liter scale.

The techniques used to develop the subject technology at the 1-2 liter scale were implemented in a 150-L stainless steel bioreactor system fitted with a scaled up hollow fiber filtration module and recirculation loop. The hollow fiber filtration module had a surface area of 2.55 meters square and a 0.2 micron pore size. Liquid was recirculated through the external perfusion loop at 8-9 liters per minute and the working volume of the bioreactor was 70 liters. At the pilot scale the perfusion medium composition was 90 millimolar amino acids, 8 g/L glucose, and 2.5 g/L sodium L-lactate (i.e., 22 mM L-lactate ion) with a final osmolality of 345 mOsm.

Figure 5A:
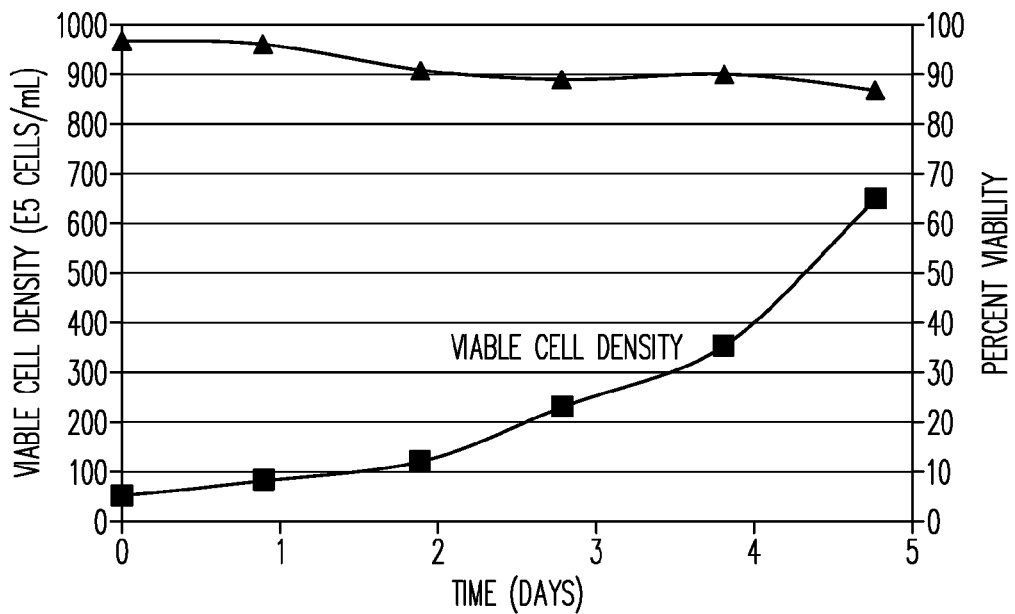
FIG. 5A shows either viable cell density (E5 or $10^5$ cells/mL) or viability (%) over time (days) of CHO cell line A in a 70-liter working volume pilot scale bioreactor using the HIPCOP method of controlling perfusion rate.
Figure 5B:
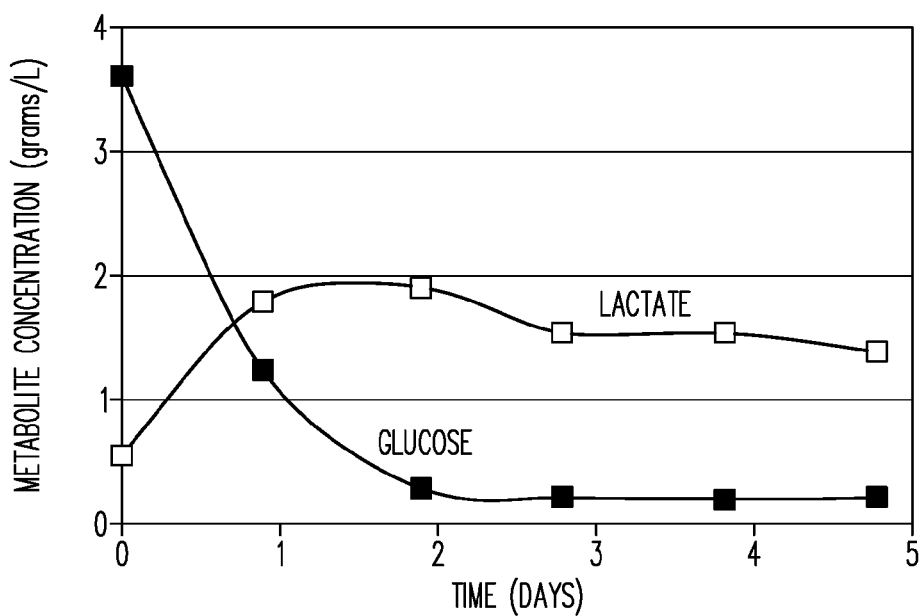
FIG. 5B shows metabolite concentration (g/L) over time (days)
Figure 5C:
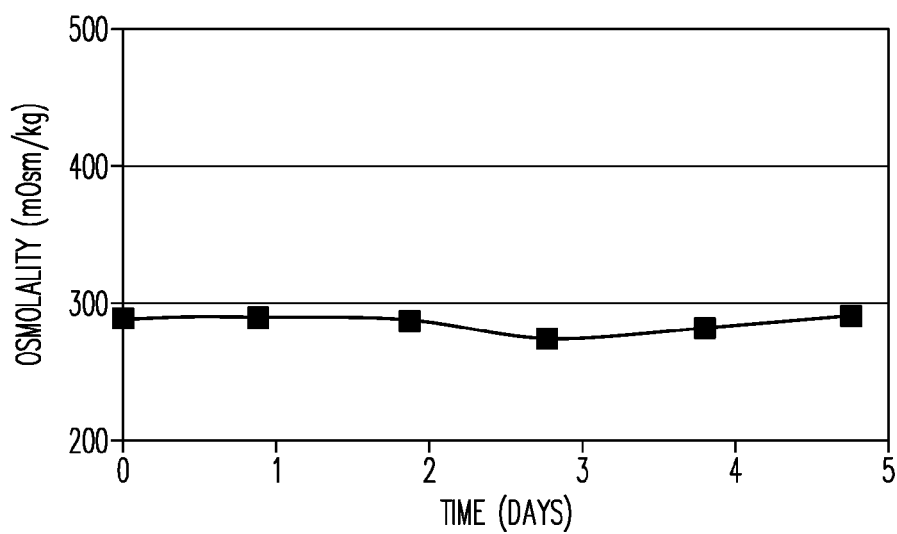
FIG. 5 (A-C) illustrates the results of the CHO cell line A growth in a 150 L bioreactor (70 L working volume) using the HIPCOP method for controlling perfusion rate (as described in Example 2).
Figure 6A:
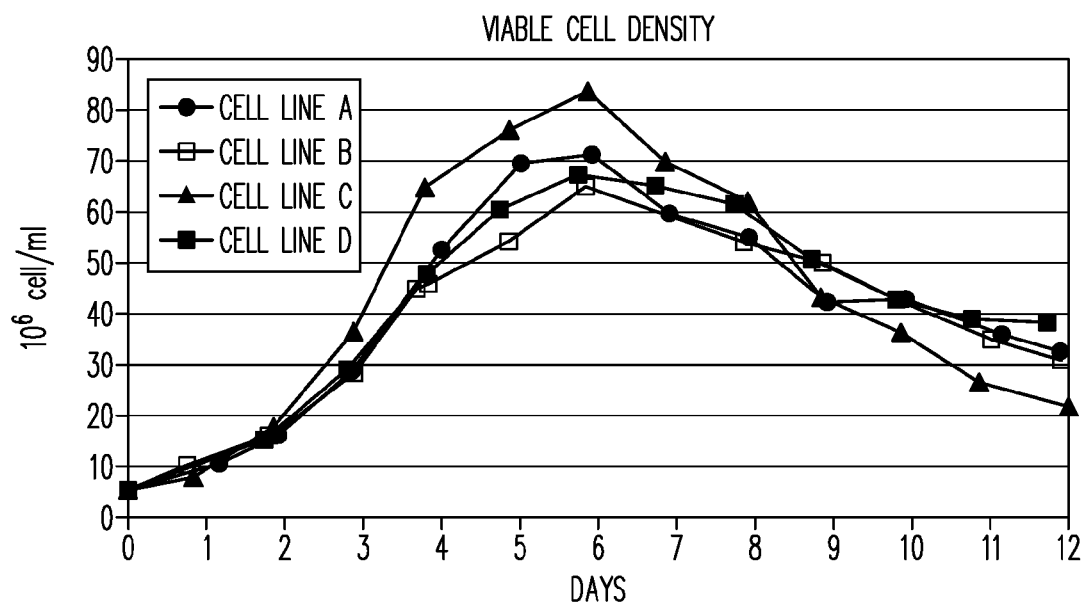
FIG. 6A shows viable cell density (E6 or $10^6$ cells/mL)
Figure 6B:
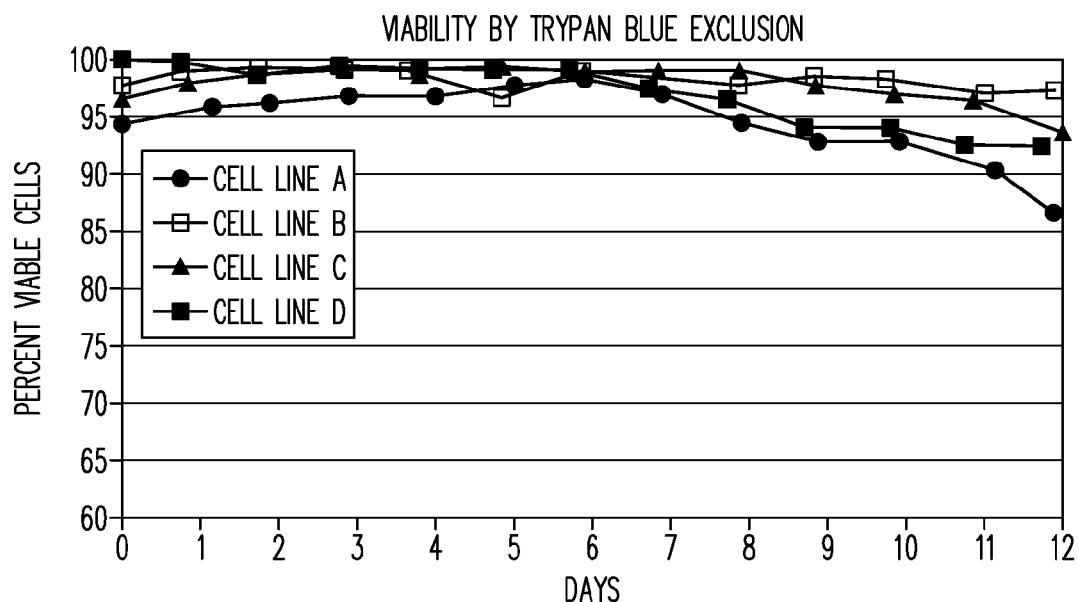
FIG. 6B shows percent viable cells as measured by trypan blue exclusion.
Figure 6C:
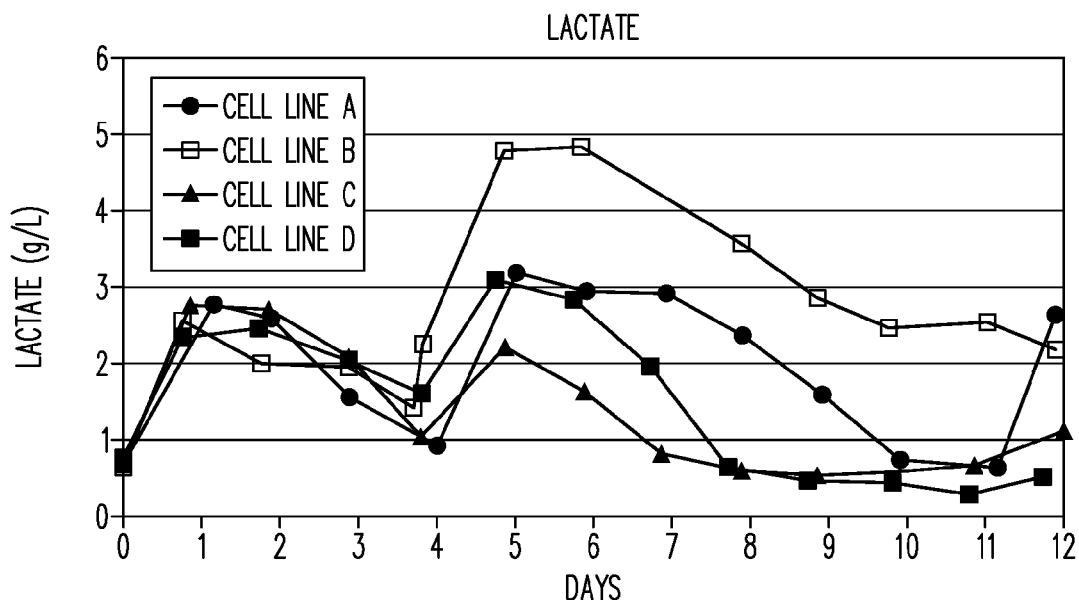
FIG. 6C shows L-lactate concentration over time.
Figure 6D:
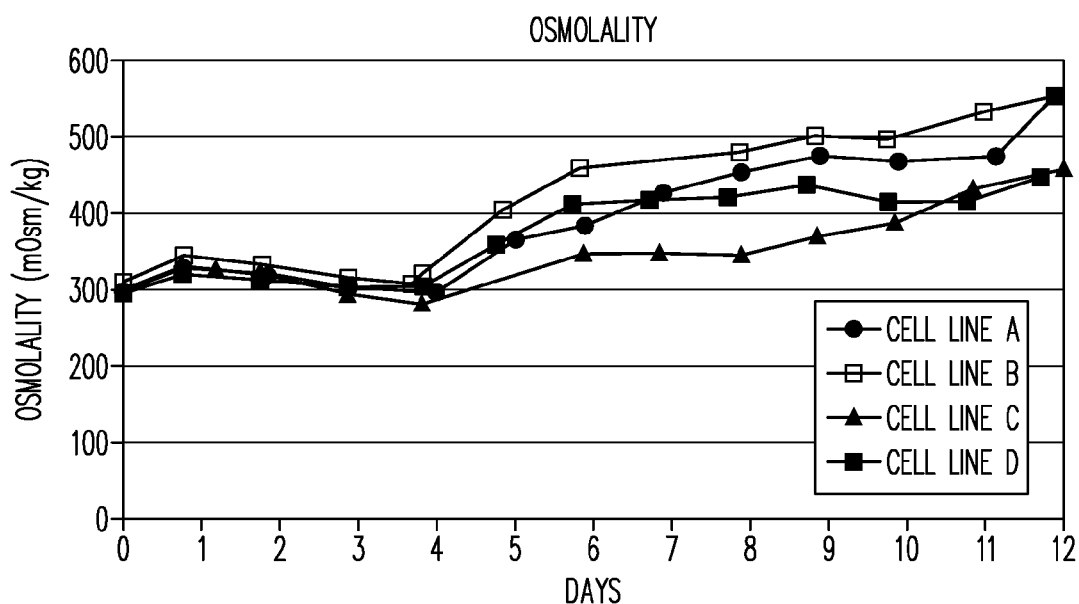
FIG. 6D shows osmotic strength over time (mOsm/kg)
Figure 6E:
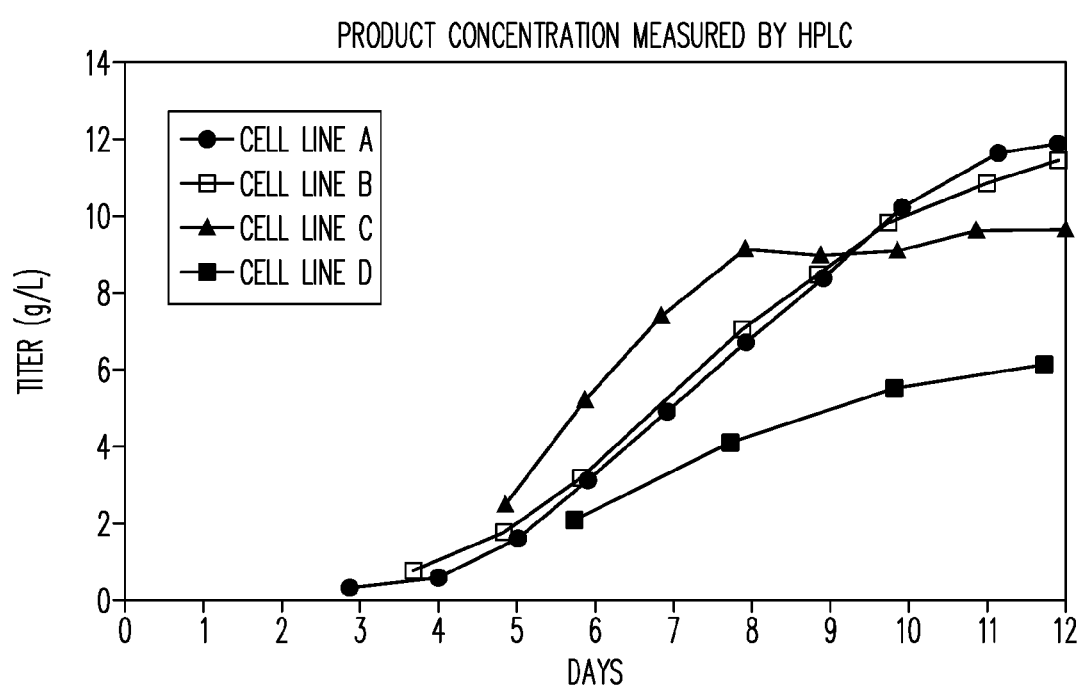
FIG. 6E shows product titer (IgG antibody) accumulation over time.

FIGS. 5A-C show the application of the HIPCOP technology with cell line A at the 70-Liter scale. Growth rates and cell viability were slightly lower at the large scale compared to the previous data from 1-2 L bioreactors. Additional optimization (to minimize cell shear damage) of the equipment used in the perfusion loop of the large scale bioreactor may be possible. The inoculation density in the pilot scale experiment was significantly higher than the previous data for cell line A from the 1-2 L bioreactors. The final cell densities reached at the pilot scale were somewhat higher than those obtained at the small scale. L-lactate and the resulting osmolality of the culture at the pilot scale were well controlled as in the small scale experiments. As expected as a result of the method of the invention, glucose levels quickly dropped and remained very low throughout the HIPCOP perfusion. It was not necessary to manually adjust the perfusion rate during the experiment at the pilot scale. Only one maximum pump speed was set and the pumps (both the feed and permeate pumps) were turned on and off by the high-end pH controller/sensor system to effectively ramp up the perfusion rate of the culture.

Example 3

Figure 7:
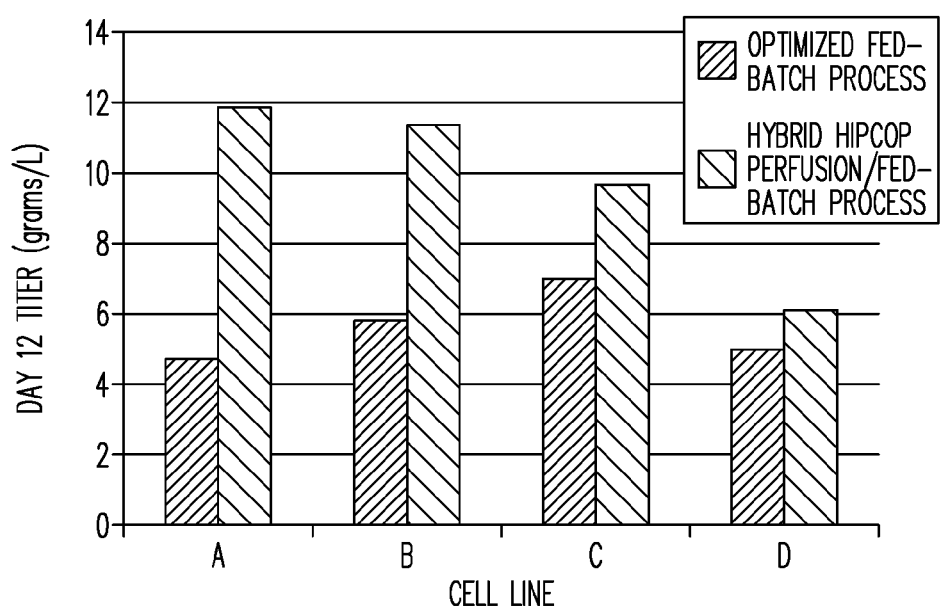
FIG. 7 illustrates the day-12 product titer (grams/liter of IgG antibody) of the hybrid perfusion/fed-batch process that used HIPCOP during the cell expansion phase in comparison to the optimized titer of the 12-day fed-batch process.

The Application of HIPCOP Technology to Additional Cell Lines in a Hybrid Perfusion/Fed-Batch Process Additional data for four different glutamine-synthetase CHO cell lines producing monoclonal antibodies are shown in FIGS. 6, 7, and 8. All data was generated with a nearly identical process with a continuous perfusion period of 4 days (perfusion ramp up using HIPCOP), after which the culture process was switched to a fed-batch process for the remainder of the 12-day culture. As such, the cells were cultured under a hybrid (i.e., HIPCOP perfusion/fed-batch) process. The perfusion medium composition was identical to that used in example 2, 90 millimolar amino acids, 8 g/L glucose, and 2.5 g/L sodium L-lactate (i.e., 22 mM L-lactate ion) with a final osmolality of 345 mOsm. As shown in FIG. 6, in this hybrid process, the cell lines reached a maximum cell density of between 67-85×10$^6$ cells/mL on days 5 and 6 with a high percentage viability of about 87 to about 97% for the entire length of the process. In some pilot-scale (~100 L) hybrid processes, cultured cells reached a density of over 95×10$^6$ cells/mL (data not shown). Titers between 6 and nearly 12 grams/liter were reached with the four different cell lines are summarized in FIG. 6E. FIG. 7 compares the titers achieved with the four CHO cell lines in an optimized fed-batch process with the titers achieved when applying the hybrid perfusion fed-batch process utilizing HIPCOP. FIG. 8 shows the very modest volumes of medium used during the HIPCOP perfusion stage of the hybrid perfusion fed-batch process. The reactor volumes are calculated based on the final volume of bioreactor that would be necessary to accommodate the feeds that occur during the fed-batch portion of the bioreactor operation (volume of feeds are also shown in FIG. 8). These results show that applying the HIPCOP technology to optimized late-stage fed-batch processes can more than double the productivity with minimal development efforts.

Example 4

The Application of HIPCOP Technology to a Continuous Perfusion Process

Figure 9A:
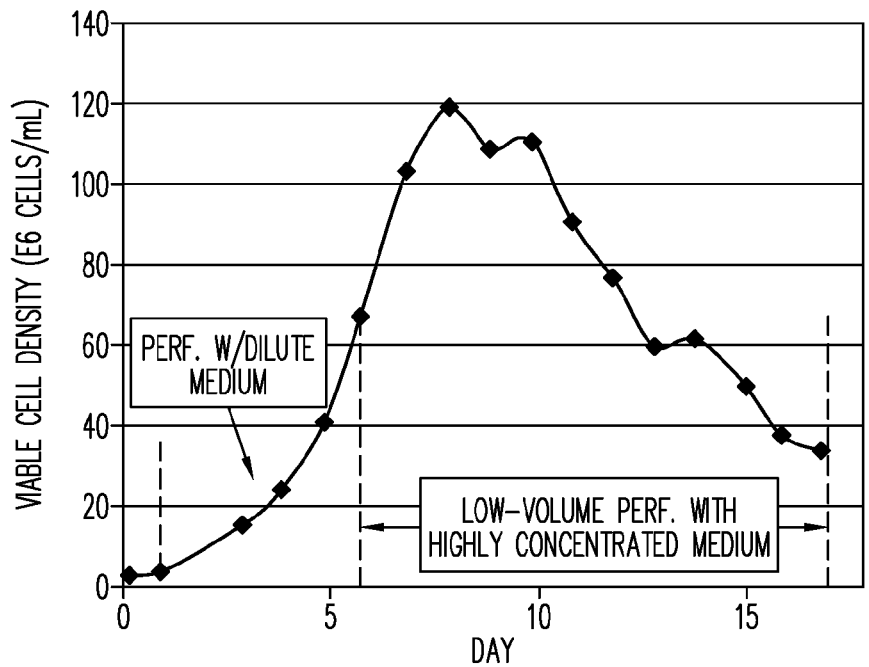
FIG. 9A-F illustrates the cell densities, cell viabilities, L-lactate concentrations, osmotic strength, product titer, and rates of perfusion as a function of time for a 2 L continuous-perfusion culture of IgG antibody-producing CHO cell line A that uses HIPCOP initially during the cell expansion phase (days 1-6) and a manually adjusted perfusion rate from day 6 to the end of the culture.
Figure 9B:
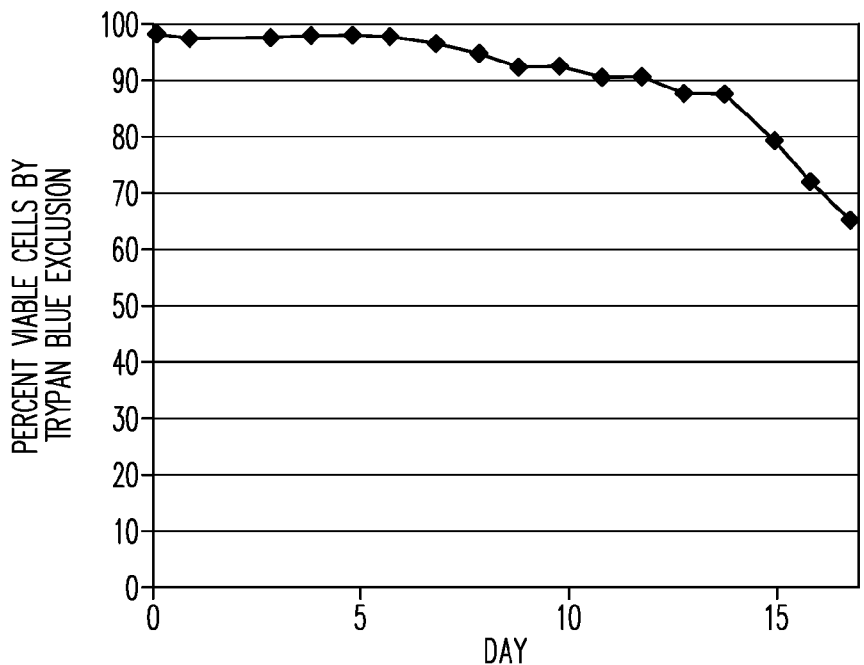
Figure 9C:
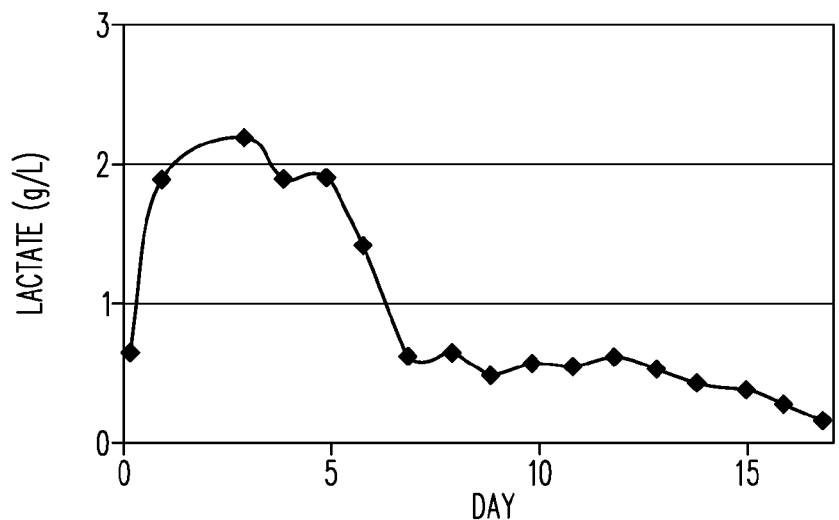
Figure 9D:
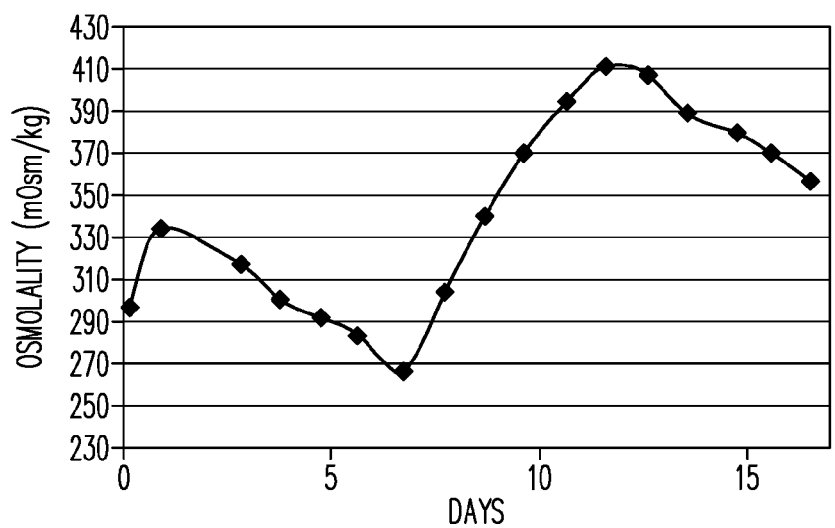

FIG. 9A tracks the viable cell density of a 2 L bioreactor with CHO cell line A in a continuous perfusion process that uses the HIPCOP technology to control perfusion for the first six days, and then reverts to a continuous perfusion with manually-controlled, but comparatively low, perfusion rates beyond day 6. The perfusion medium used during the first six days was identical in make up to that used in example 3 (90 millimolar amino acids, 8 g/L glucose, and 2.5 g/L sodium L-lactate (i.e., 22 mM L-lactate ion) with a final osmolality of 345 mOsm). From day 6 to day 17 the culture was perfused using a highly concentrated perfusion nutrient solution of 600 millimolar amino acids (90 grams/liter glucose, 0 g/L sodium L-lactate, final osmolality of approximately 1300 mOsm/kg) and a saline diluent (2.0 g/L sodium bicarbonate, 2.4 g/L polyvinyl alcohol [a shear protectant], 20 mM potassium chloride, and 80 mM sodium chloride, pH of 7.10, final osmolality of 250 mOsm/kg) in varying ratios as indicated in FIG. 9F. In later experiments (data not shown) it was determined that similar results could be obtained when the sodium bicarbonate and the polyvinyl alcohol were removed from the saline diluent. In this case the levels of sodium chloride were increased to achieve a similar final osmotic strength of 250 mOsm/kg (20 mM potassium chloride and 105 mM sodium chloride) for the diluent. To minimize volumes of liquid that might need to be transported, at the large scale it might be optimal to use a nearly saturated solution of potassium chloride and sodium chloride with a molar ratio of approximately 1:5 respectively and dilute as necessary with additional water.

Viable cell densities in this system reached extremely high levels, and were sustained over 100×10$^6$ cells/milliliter for several days (FIG. 9A). Cell viabilities were also high as shown in FIG. 9B. L-lactate levels were well controlled and remained at or below 2 grams/liter during the expansion phase of the culture as the HIPCOP perfusion was operating as shown in FIG. 9C. Osmolality was also well controlled as shown in FIG. 9D. The control of osmolality was facilitated by the variable rate addition of the saline diluent solution that was initiated on day 6 and ramped up relative to the perfusion rate of the concentrated nutrient perfusion medium towards the conclusion of the experiment (FIG. 9F). The rates of perfusion achieved by adding the saline diluent and concentrated perfusion nutrient solution were manipulated in an effort to simultaneously add sufficient nutrients to sustain the cell biomass and produce the protein of interest, to facilitate the removal of the protein of interest from the bioreactor through the cell retention hollow-fiber filtration device and into the continuous downstream process at a controlled rate within a reasonably narrow band of total mass/day, and also to maintain the osmotic strength of the culture near to an optimal window of 250-350 mOsm.

Figure 9E:
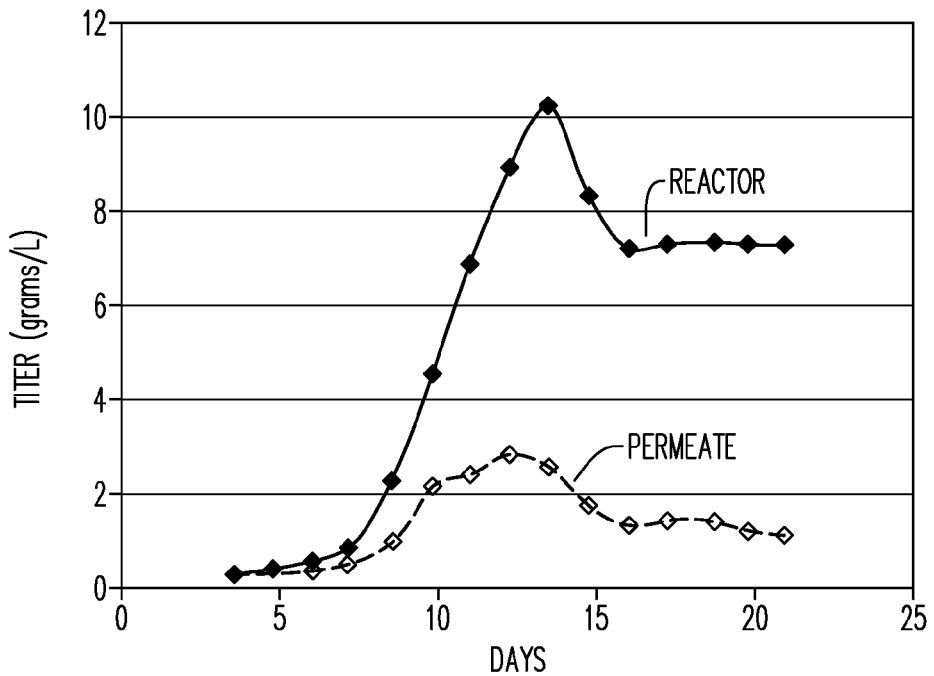
Figure 9F:
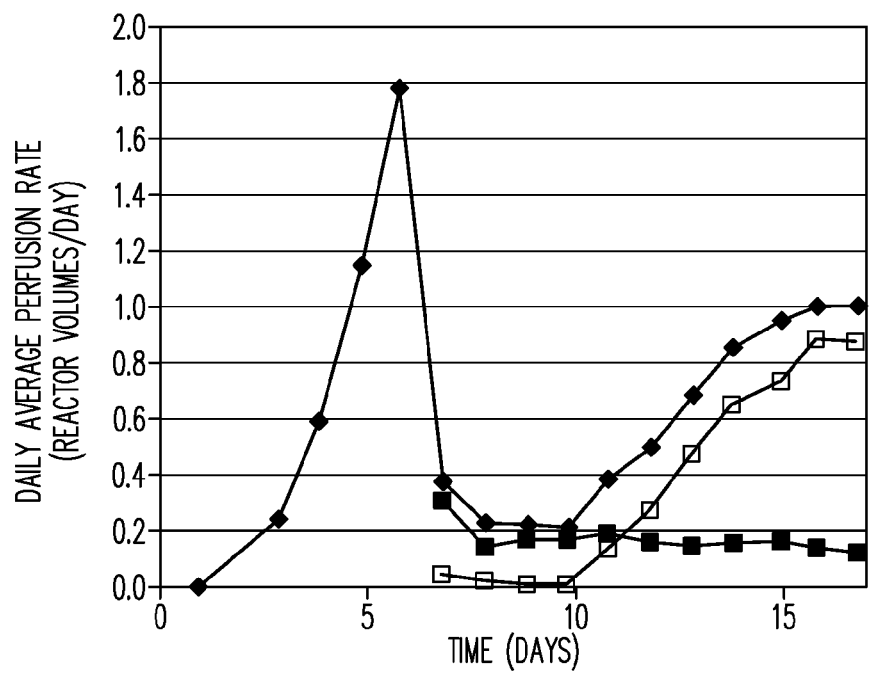

FIG. 9E shows the titer achieved in the bioreactor and that in the permeate leaving the bioreactor system through the hollow-fiber filtration device. Likely due to a build-up of protein on the surface of the micro-filtration hollow-fiber module, the concentration of antibody in the bioreactor becomes higher than that leaving in the permeate. This selective concentration of the protein of interest inside the bioreactor may be undesirable if a continuous downstream process is used. There may be minor modifications to the cell retention system which could be used to eliminate or minimize this problem (larger microfiltration pore size, larger filter area, alternative microfiltration materials of construction, more aggressive tangential flow, back-flushing of the filter) or methods of cell retention that are less prone or impervious to production retention might be employed (spin filters, acoustic wave cell settling devices, inclined-plane gravity cell-settling devices).

Figures 10, 11:
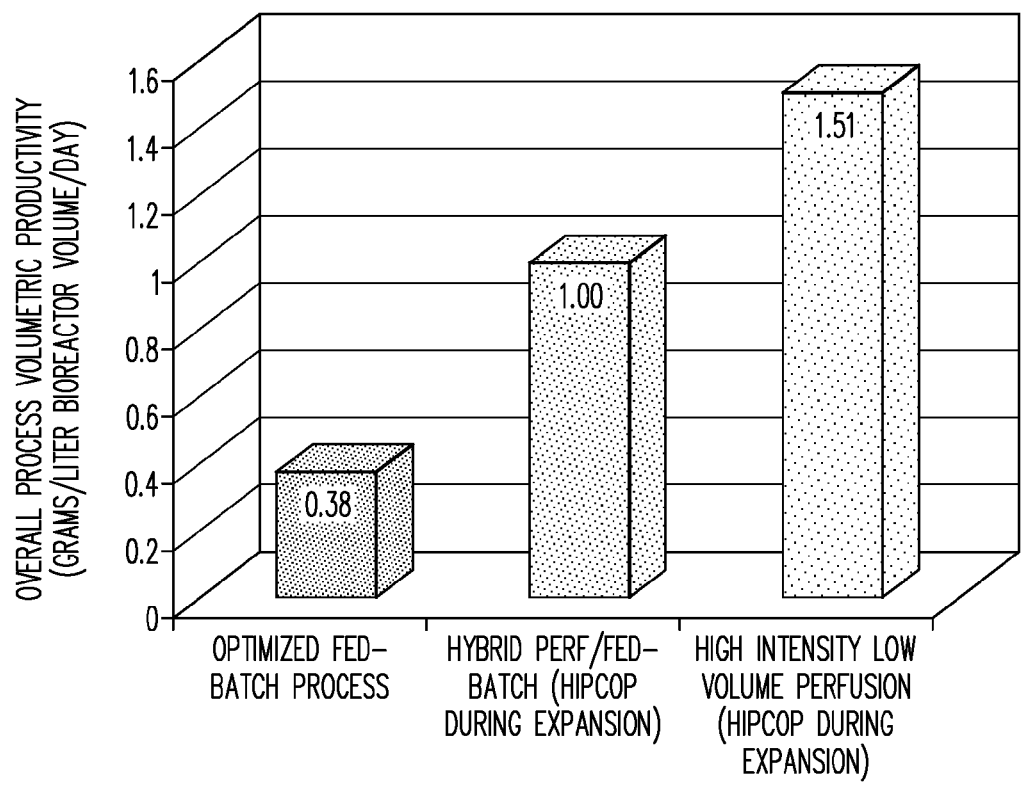
FIG. 10 is a table listing the overall volumetric productivity as calculated assuming all product of interest is captured from a final harvest of the bioreactor and the permeate collected from days 6-17 using the entire length of the process (17 days) as the divisor. Also listed are the total volumes of initial perfusion medium (days 1-6), concentrated nutrient perfusion medium (days 6-17) and saline diluent (days 6-17) used in the experiment of FIG. 9A-F.
FIG. 11 is a bar graph illustrating the increases in overall process volumetric productivity when compared with an optimized fed-batch process (first bar from left, a 12-day process) that can be achieved using the HIPCOP technology paired with either a hybrid perfusion fed-batch operational mode ($2^{nd}$ bar from left, a 12-day process), or a continuous perfusion operational mode (high-intensity, low volume perfusion, a 17-day process, $3^{rd}$ bar from left). All data in this figure was collected using cell line A as described in earlier figures and in the examples. The overall process volumetric productivity calculations assume that product leaving the bioreactor system in the permeate, and that remaining in the bioreactor can be utilized. The material in the bioreactor presumably would be captured by a final harvest step at the end of the process. The calculations do not include the product lost to the permeate stream during the expansion phase while comparatively dilute perfusion medium is being utilized (while the HIPCOP technology is in operation, day 0-4 for the hybrid perfusion fed-batch process, and day 0-6 for the continuous perfusion process). Furthermore, the calculations utilize the entire batch length (from inoculation to termination at harvest) as the divisor.

FIG. 10 list several important parameters for the continuous perfusion process (high-intensity, low-volume perfusion). The table lists the overall volumetric productivity (grams/Liter of reactor volume/day) of the process, and the total volumes of the various perfusion media utilized during the entire experiment (in reactor volumes). As evidenced by the data in the table, the volumetric productivity is very high and the overall volumes of perfusion medium are very modest for the continuous perfusion process which uses HIPCOP during expansion (days 0-6) and later uses the saline diluent to control osmotic strength when the highly concentrated perfusion medium is utilized from days 6-17. FIG. 11 compares the volumetric productivity of both the hybrid perfusion fed-batch (second bar from the left) and the continuous perfusion process (third bar from the left), both processes using HIPCOP during the cell expansion phase, to the optimized fed-batch process (first bar on the left) that had been developed for model cell line A. As seen in the figure, the continuous perfusion process (high intensity low volume perfusion) using HIPCOP during the expansion phase has nearly a 4-fold increase in volumetric productivity when compared to the optimized fed-batch process.

In the high intensity low volume perfusion process, a diluent liquid is added to the bioreactor during the later stages of the perfusion culture when the concentrated perfusion medium is being added to the bioreactor. For example, the diluent liquid (a solution of saline) of appropriate concentration (e.g., 2.0 g/L sodium bicarbonate, 2.4 g/L polyvinyl alcohol, 20 mM potassium chloride, and 80 mM sodium chloride) was added to the bioreactor. Using a diluent liquid (e.g., saline) in combination with the concentrated perfusion medium allows for perfusion rates as low as 0.05-0.30 reactor volumes per day for the concentrated perfusion medium. The addition of the diluent will also facilitate the flushing of the product material out of the bioreactor, particularly if a continuous downstream process is linked directly to capture the continuously delivered upstream harvest material, and if the protein being produced is highly labile. Additionally, in order to avoid an excessively large downstream it is also advantageous to control the mass per day of product entering the downstream process within a small range. This can also be facilitated by manipulating the flow rate of the diluent, e.g., saline. The addition of the diluent can also advantageously facilitate the control over or the maintenance of the osmotic strength of the bioreactor environment close to the physiological range of 250-350 mOsm.

Example 5

Use of HIPCOP Technique with High Sodium Bicarbonate in Perfusion Medium and a DG44 Derived CHO Cell Line Expressing a Recombinant Protein of ~130 kDa The method of using additional sodium bicarbonate in the perfusion medium in place of sodium-L or sodium D/L lactate was tested with an additional cell line, cell line "E". The perfusion medium contained 90 millimolar amino acids, 8 grams/L glucose, 10 millimolar glutamine, 3.87 grams/L sodium bicarbonate (which is approximately 1.87 grams/L additional that would have been in the perfusion medium if sodium L-lactate were being used at 2.5 grams/L), with a final osmotic strength of 330 mOsm/kg. The initial basal medium in this experiment consisted of 120 millimolar amino acids, 6 grams/L glucose, 10 millimolar glutamine, and 10 mg/L recombinant insulin. Cells were inoculated at approximately $10 \times 10^6$ viable cells/ml. Cell growth was very fast and the perfusion was initiated by the cells at approximately 23 hours after inoculation. Perfusion continued for approximately 29 hours over which time the culture used a total of 0.85 reactor volumes of perfusion medium. The perfusion rate in the last 4 hours of perfusion was approximately 1.4 reactor volumes per day.

Figure 12A:
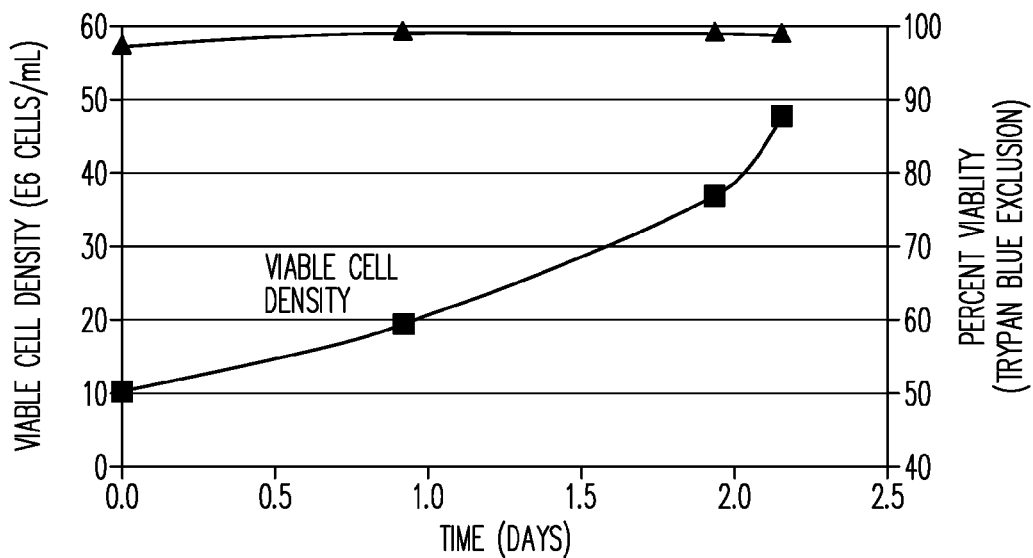
FIG. 12A shows either viable cell density (E6 cells/mL) or viability (%) over time (days)
Figure 12B:
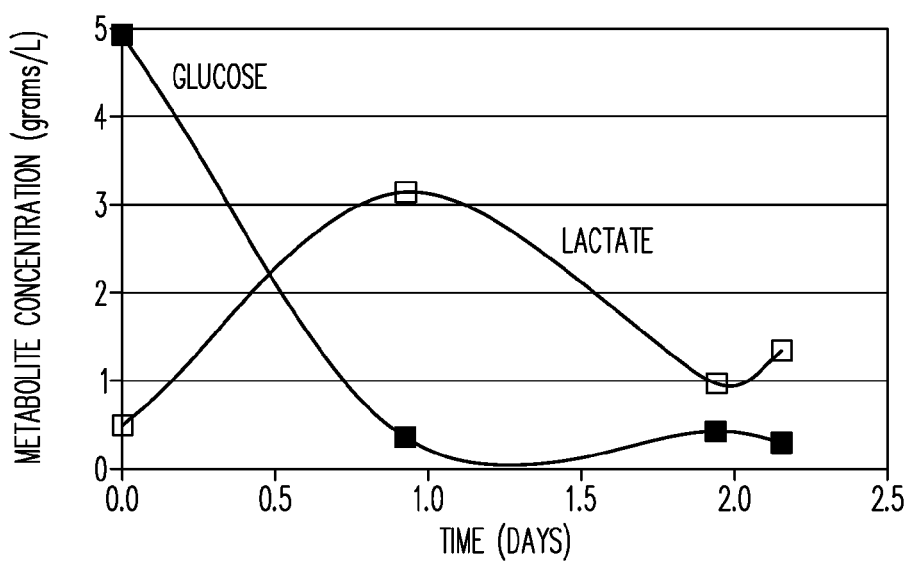
FIG. 12B shows metabolite concentration (g/L) over time (days)
Figure 12C:
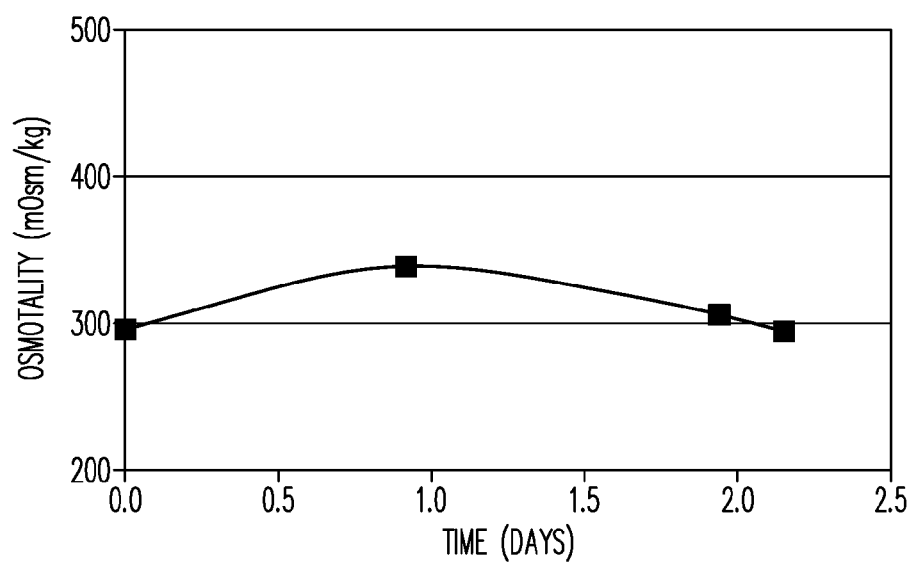
FIG. 12C shows osmolality (mOsm/kg) over time (days).

As in the case with the previous examples, the HIPCOP method of cell-controlled perfusion worked well with this cell line. Cells grew to $47 \times 10^6$ viable cells/ml within 52 hours after inoculation (FIG. 12A). FIG. 12B shows that glucose was quickly consumed and then maintained at a low concentration using the subject technology. Additionally, FIG. 12B shows that lactate was controlled at a low level, ending at about 1.3 grams/liter. FIG. 12C shows that the osmotic strength of the culture was also maintained very close to a physiologically ideal range near 300 mOsm/kg throughout the time the perfusion was being performed.

Example 6

Use of HIPCOP Technique with High Sodium Bicarbonate in Perfusion Medium and a Glutamine-Synthetase CHO Cell Line Expressing a Recombinant Immunoglobulin G The method of using additional sodium bicarbonate in the perfusion medium in place of sodium-L or sodium D/L lactate was tested with an additional cell line, cell line "B". The perfusion medium contained 90 millimolar amino acids, 10 grams/L glucose, 3.87 grams/L sodium bicarbonate (which is approximately 1.87 grams/L additional than would have been in the perfusion medium if sodium L-lactate were being used at 2.5 grams/L), with a final osmotic strength of 366 mOsm/kg. The initial basal medium in this experiment consisted of 120 millimolar amino acids, 4 grams/L glucose. Cells were inoculated at approximately $1.2 \times 10^6$ viable cells/ml. Perfusion was initiated by the cells at approximately 2.3 days after inoculation. Perfusion continued for approximately 3.7 days over which time the culture used a total of 2.09 reactor volumes of perfusion medium. The perfusion rate in the last 4 hours of perfusion was approximately 1.23 reactor volumes per day.

Figure 13A:
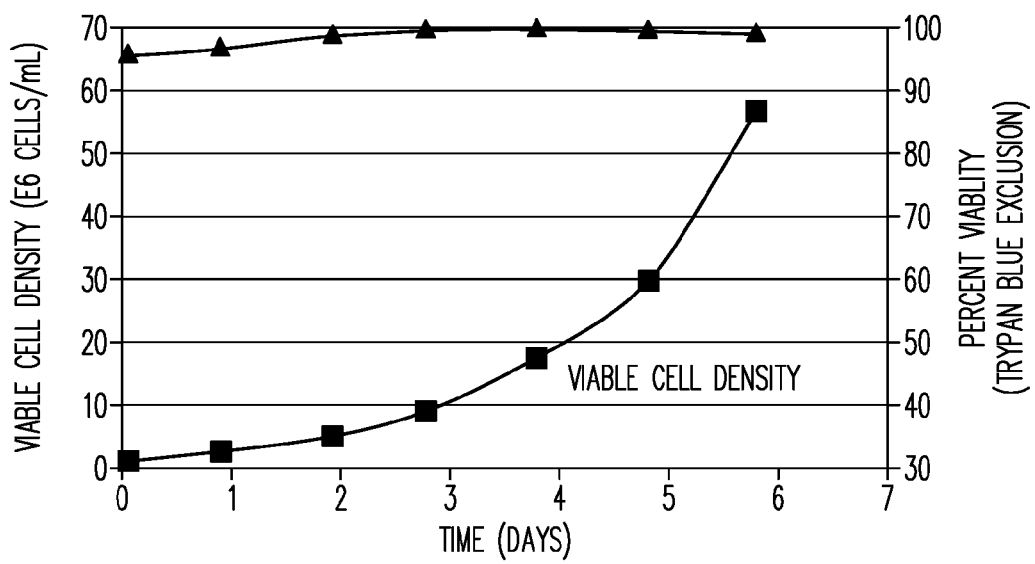
FIG. 13A shows either viable cell density (E6 cells/mL) or viability (%) over time (days)
Figure 13B:
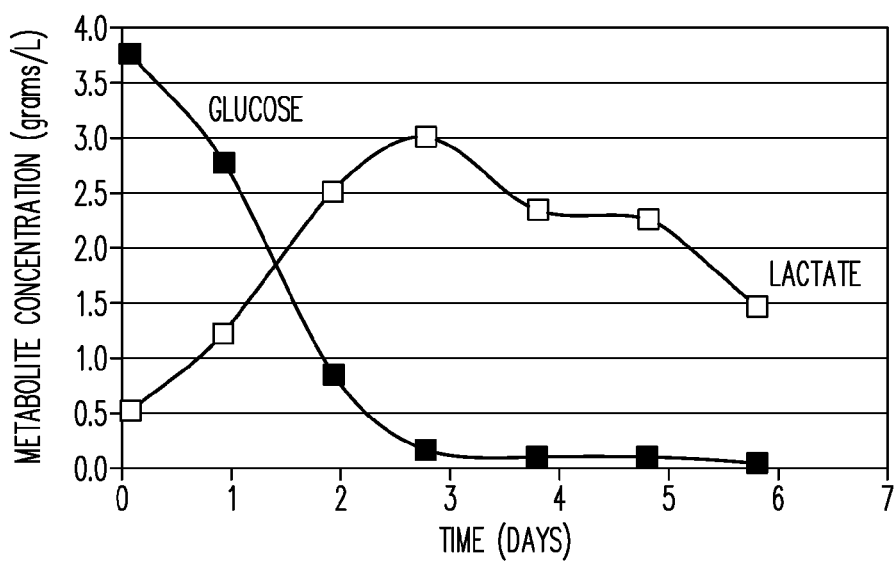
FIG. 13B shows metabolite concentration (g/L) over time (days)
Figure 13C:
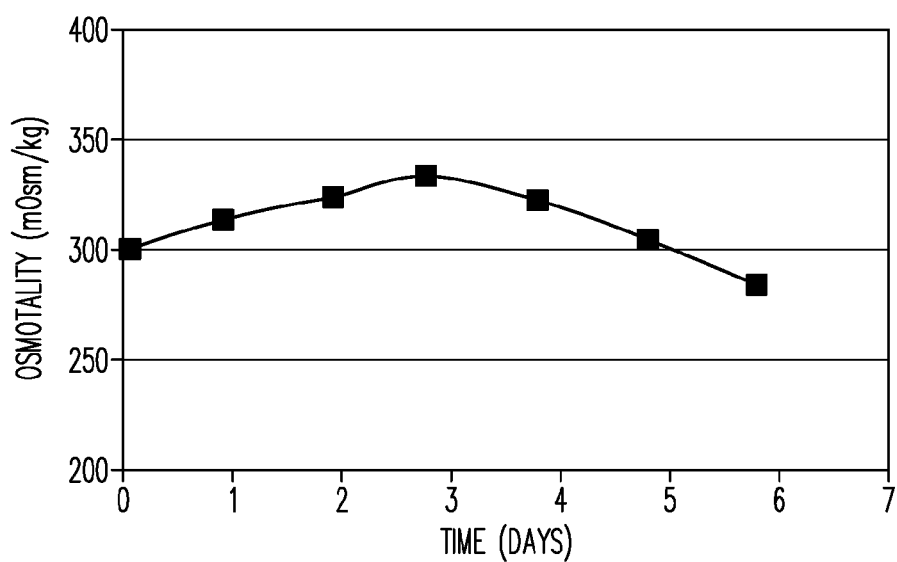
FIG. 13C shows osmolality (mOsm/kg) over time (days).

As in the case with the previous examples, the HIPCOP method of cell-controlled perfusion worked well with this cell line. Cells grew to $57 \times 10^6$ viable cells/ml within 5.8 days after inoculation (FIG. 13A). FIG. 13B shows that glucose was quickly consumed and then maintained at a low concentration using the subject technology. Additionally, FIG. 13B shows that lactate was controlled at a low level, ending at about 1.47 grams/liter. FIG. 13C shows that the osmotic strength of the culture was also maintained very close to a physiologically ideal range near 300 mOsm/kg throughout the time the perfusion was being performed.

Example 7

Use of HIPCOP Technique with Sodium Carbonate Feed and a Glutamine-Synthetase CHO Cell Line Expressing a Recombinant Immunoglobulin G This is an example of the use of HIPCOP to control the perfusion rate of a 'sustainable' continuous perfusion bioreactor. The example starts with a perfusion reactor operating at a near steady-state condition with HIPCOP allowing the cells to control their own perfusion rate with sodium-L-lactate in the perfusion medium. A change is then made to the composition of that perfusion medium, removing sodium-L-lactate.

The method of using a separate carbonate feed in place of sodium-L or sodium D/L lactate in the perfusion medium was tested with cell line "B". The data for two steady-states are shown. The perfusion medium for steady-state 1 contained 110 millimolar amino acids, 10 grams/L glucose, 2.6 g/L sodium lactate, 2.0 grams/L sodium bicarbonate, with a final osmotic strength of 405 mOsm/kg. The perfusion medium for steady-state 2 contained 110 millimolar amino acids, 12.1 grams/L glucose, 2.0 grams/L sodium bicarbonate, with a final osmotic strength of 403 mOsm/kg. Note that the total carbon source with respect to glucose and lactate were kept approximately the same between the perfusion media used during both steady-states. Perfusion was maintained by the cells and a cell-bleed was adjusted once daily to maintain the viable cell-density at a target of $40 \times 10^6$ viable cells/ml. The continuous steady-state perfusion rate that the cells have 'determined' is approximately 1.0 reactor volumes per day. During steady-state 1, no carbonate was added. During steady-state 1 the cells are clearly consuming a significant fraction of the lactate that is entering in the perfusion medium since the residual levels of lactate in the bioreactor are lower than that in the perfusion medium. They presumably are consuming the lactate as lactic acid. The consumption of lactic acid by the cells maintains a continuous upward influence on the pH of the culture and allows the HIPCOP technology to function properly. When steady-state 2 is initiated this continuous upward influence on the pH of the culture is now instead provided through the semi-continuous addition of a 1 molar carbonate solution (in this case the carbonate is a mixture of sodium and potassium carbonate in the molar ratio of 0.94 sodium:0.06 potassium)

at a rate of approximately 8.7 mL per liter of bioreactor volume. Therefore the addition of 1 molar carbonate enters at a ratio of 8.7 mL per 1 liter of perfusion medium utilized.

Figure 14A:
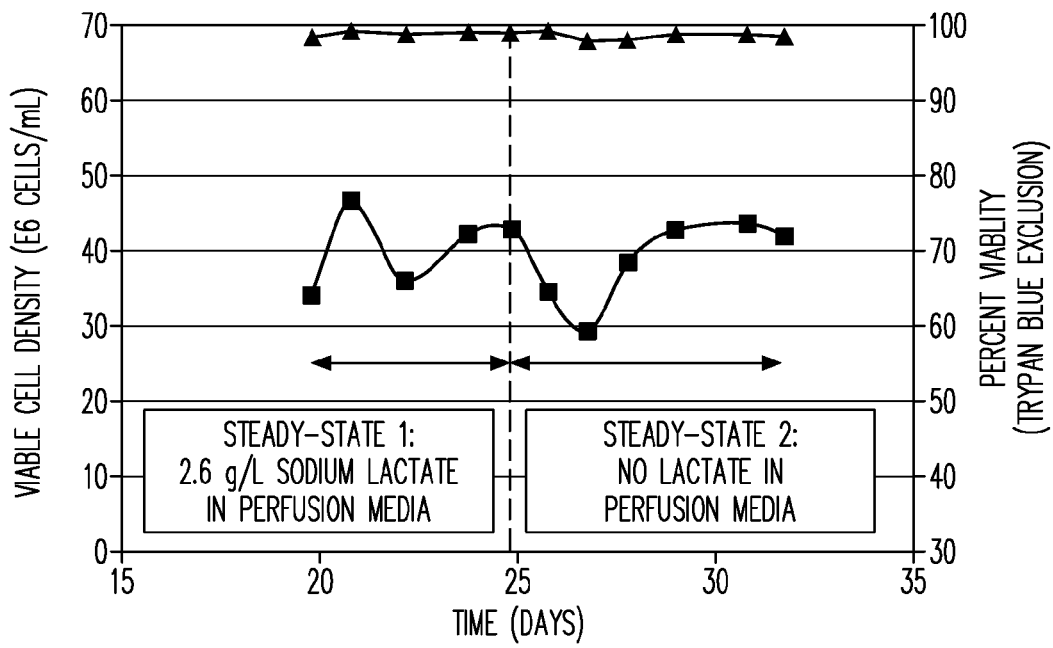
FIG. 14A shows either viable cell density (E6 cells/mL) or viability (%) over time (days)
Figure 14B:
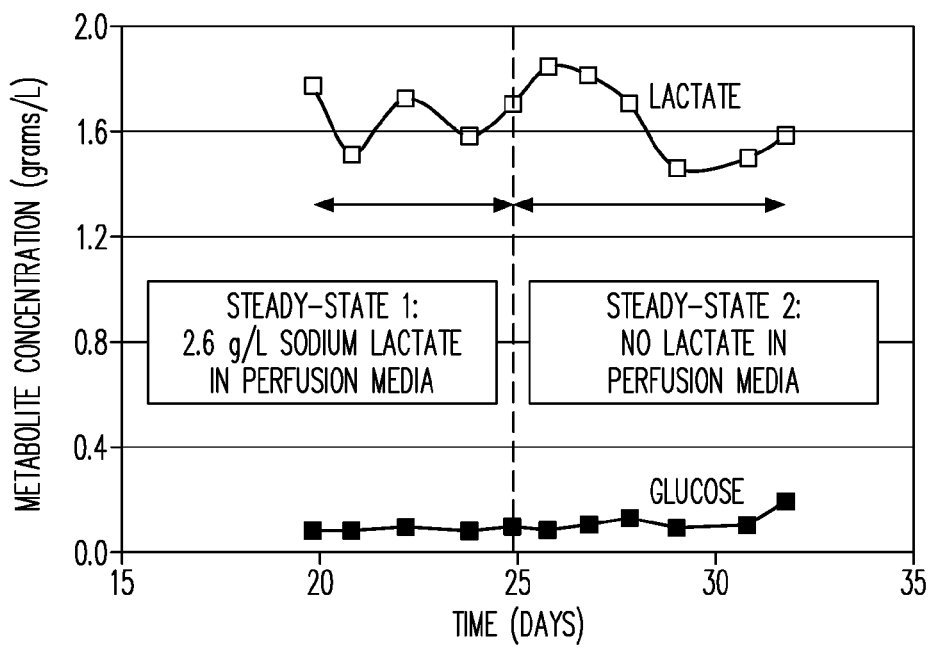
FIG. 14B shows metabolite concentration (g/L) over time (days)
Figure 14C:
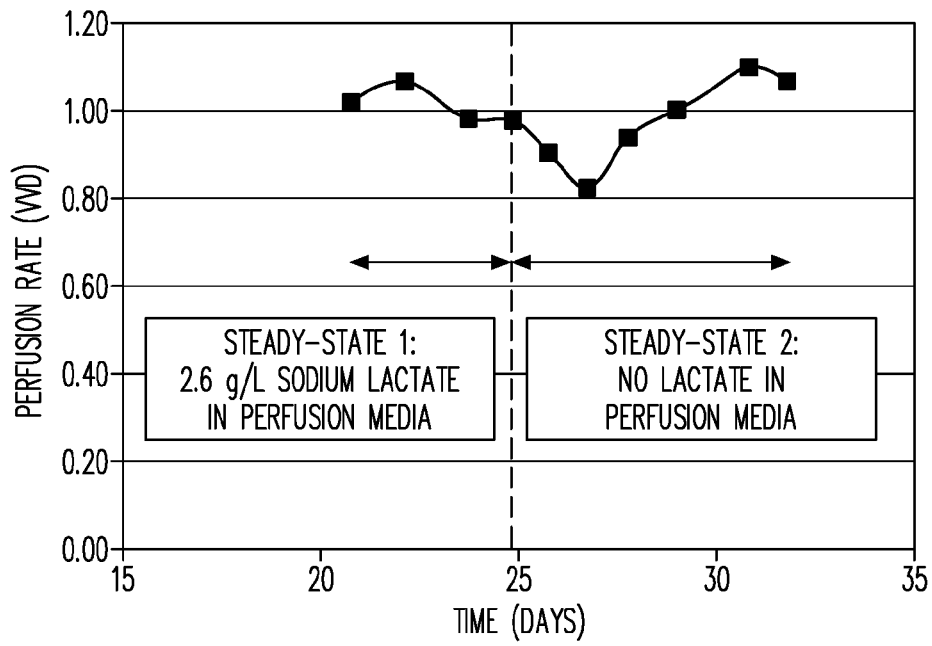
FIG. 14C shows daily average perfusion rate (VVD) over time (days)
Figure 14D:
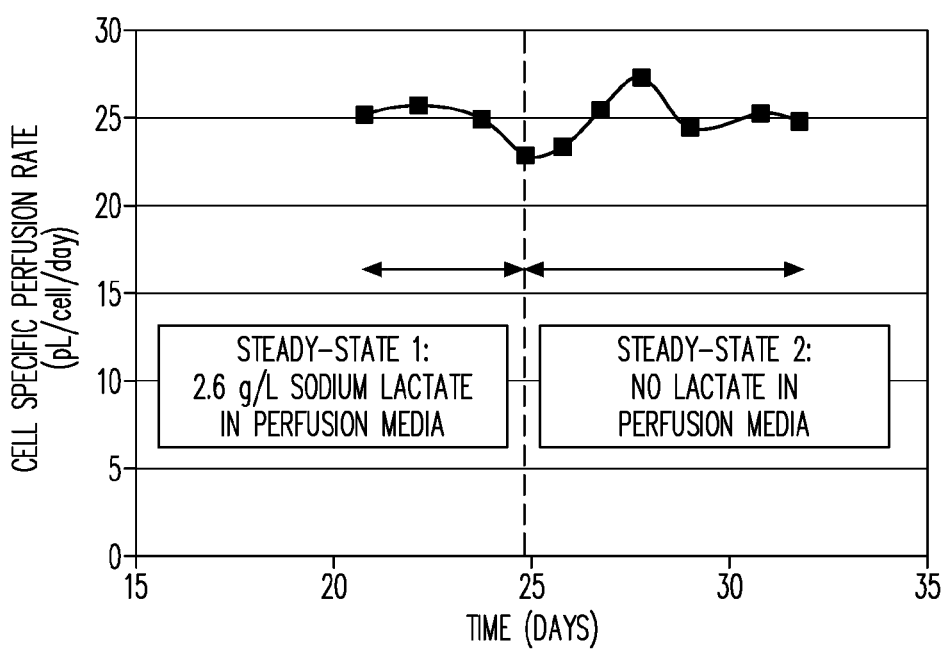
FIG. 14D shows cell-specific perfusion rate (pL/cell/day) over time (days)
Figure 14E:
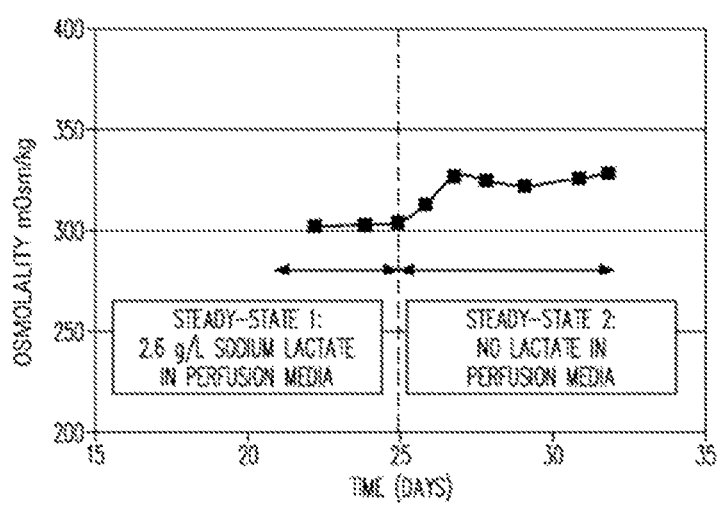
FIG. 14E shows osmolality (mOsm/kg) over time (days).

As in the case with the previous examples, the HIPCOP method of cell-controlled perfusion worked well with this cell line during both steady-states. The average perfusion rate and cell-specific perfusion rate during each steady-state were 1.0 reactor volumes per day and 25 picoliters/cell/day, respectively (FIGS. 14C & 14D). FIG. 14B shows that during both steady-states, lactate was maintained within a range of 1.5-1.8 g/L. FIG. 14E shows that the osmotic strength of the culture was maintained in a physiologically ideal range near 300 mOsm/kg. There was a slight change in the steady-state osmotic strength of the culture from steady-state 1 to steady-state 2, this may have been due to the additional sodium entering the bioreactor in the 1 molar carbonate solution that was not completely accounted for when the perfusion medium composition was designed and prepared (a small fraction of the sodium chloride normally used in the perfusion medium preparation should have been excluded).

While in the current example a mixture of sodium and potassium carbonate added continuously were used to provide the upward pressure on pH that the consumption of lactic acid from the perfusion medium would have supplied if sodium-L-lactate were in the perfusion medium, presumably any appropriate non-toxic basic substance added in a continuous or semi-continuous manner to the culture could provide the same effect. Examples of such bases could include sodium or potassium hydroxide, among many others.

While the subject technology has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of the subject technology, and are covered by the following claims.

INDUSTRIAL APPLICABILITY

The device and methods disclosed herein are useful for perfusion biomaufacturing, and thus for improving industrial methods for manufacturing recombinant, therapeutic proteins.

What is claimed is:

1. A continuous perfusion culture process, comprising:
   a) monitoring pH in a cell culture with a pH sensor, wherein the cell culture comprises mammalian cells;
   b) delivering fresh medium and removing permeate when the pH is above a predetermined value; and
   c) deactivating the medium delivery and the permeate removal when the pH is below the predetermined value,
   wherein the fresh medium comprises glucose and L-lactate, and
   wherein the cells control their perfusion rate over the entire continuous perfusion period by taking up lactic acid when the glucose level in the cell culture becomes limiting, and excreting lactic acid when the glucose level in the cell culture becomes non-limiting.

2. The process according to claim 1, wherein the L-lactate is present in the fresh medium in an amount of about 0.1 g/L to 7.0 g/L.

3. The process according to claim 1, wherein the L-lactate is sodium L-lactate or potassium L-lactate.

4. The process according to claim 1, wherein the fresh medium further comprises:
   amino acids.

5. The process according to claim 1, wherein the fresh medium comprises:
   (a) between about 0.5 and 40 g/L glucose;
   (b) between about 0.1 and 7 g/L L-lactate; and
   (c) amino acids in a ratio of between about 0.25 and 1.0 mole glucose to mole amino acids.

6. The process according to claim 4, wherein the amino acids and glucose are provided in an amount equal to 70 mM amino acids and 5.3 grams of glucose per liter of medium or at ratios selected from the group consisting of 60:4.2; 90:8; 100:12; 120:13; 240:42 and 380:70 mM amino acids: grams/L glucose per liter of medium.

7. The process according to claim 1, wherein the predetermined value is about pH 7.

8. The process according to claim 1, wherein during the course of culturing the cells the lactate concentration of the cell culture drops to 2 g/L after 3 days of culture, and the lactate concentration remains below 2 g/L for the duration of the continuous perfusion process.

* * * * *